(12) United States Patent
Bourang et al.

(10) Patent No.: US 11,000,392 B2
(45) Date of Patent: May 11, 2021

(54) PARTIALLY CRIMPED STENT

(71) Applicant: ADVANCED BIFURCATION SYSTEMS INC., Los Angeles, CA (US)

(72) Inventors: Henry Bourang, Turlock, CA (US); Mehran Khorsandi, Los Angeles, CA (US)

(73) Assignee: Advanced Bifurcation Systems Inc., Livermore, CA (US)

( * ) Notice: Subject to any disclaimer, the term of this patent is extended or adjusted under 35 U.S.C. 154(b) by 434 days.

(21) Appl. No.: 15/661,975

(22) Filed: Jul. 27, 2017

(65) Prior Publication Data
US 2017/0319366 A1 Nov. 9, 2017

Related U.S. Application Data

(60) Continuation of application No. 14/317,387, filed on Jun. 24, 2014, now Pat. No. 9,737,424, which is a division of application No. 13/071,149, filed on Mar. 24, 2011, now Pat. No. 8,821,562, which is a continuation of application No. PCT/US2009/058505, filed on Sep. 25, 2009.
(Continued)

(51) Int. Cl.
*A61F 2/954* (2013.01)
*A61F 2/856* (2013.01)
(Continued)

(52) U.S. Cl.
CPC .............. *A61F 2/954* (2013.01); *A61F 2/856* (2013.01); *A61F 2/958* (2013.01); *A61F 2/91* (2013.01);
(Continued)

(58) Field of Classification Search
CPC .. A61F 2/865; A61F 2/91; A61F 2/954; A61F 2/958; A61F 2002/9522; A61F 2230/001; A61F 2250/0098
See application file for complete search history.

(56) References Cited

U.S. PATENT DOCUMENTS

| | | |
|---|---|---|
| 4,069,825 A | 1/1978 | Akiyama |
| 4,468,224 A | 8/1984 | Enzmann et al. |

(Continued)

FOREIGN PATENT DOCUMENTS

| | | |
|---|---|---|
| CN | 1441654 A | 9/2003 |
| CN | 1788977 A | 6/2006 |

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages.
(Continued)

*Primary Examiner* — Jacob J Cigna
(74) *Attorney, Agent, or Firm* — Schwegman Lundberg & Woessner, P.A.

(57) ABSTRACT

A crimping method that crimps a stent over multiple catheters. The method includes differentially crimping a stent on certain portions of a balloon catheter so that a second catheter can be threaded through the uncrimped portion of the stent and exit through the links of a conventional stent design or through a specific hole in the stent designed for a branched vessel.

6 Claims, 13 Drawing Sheets

Related U.S. Application Data

(60) Provisional application No. 61/194,346, filed on Sep. 25, 2008.

(51) Int. Cl.
- *A61F 2/958* (2013.01)
- *A61F 2/91* (2013.01)
- *A61F 2/95* (2013.01)

(52) U.S. Cl.
CPC ....... *A61F 2/9522* (2020.05); *A61F 2230/001* (2013.01); *A61F 2250/0098* (2013.01)

(56) References Cited

U.S. PATENT DOCUMENTS

| | | | |
|---|---|---|---|
| 4,512,338 A | 4/1985 | Balko et al. | |
| 4,564,014 A | 1/1986 | Fogarty et al. | |
| 4,580,568 A | 4/1986 | Gianturco | |
| 4,681,110 A | 7/1987 | Wiktor | |
| 4,690,684 A | 9/1987 | McGreevy et al. | |
| 4,733,665 A | 3/1988 | Palmaz et al. | |
| 4,739,762 A | 4/1988 | Palmaz et al. | |
| 4,762,129 A | 8/1988 | Bonzel | |
| 4,770,176 A | 9/1988 | McGreevy et al. | |
| 4,775,337 A | 10/1988 | Van Wagener et al. | |
| 4,776,337 A | 10/1988 | Palmaz et al. | |
| 4,886,062 A | 12/1989 | Wiktor | |
| 4,891,225 A | 1/1990 | Langer et al. | |
| 4,988,356 A | 1/1991 | Crittenden et al. | |
| 4,994,066 A | 2/1991 | Voss | |
| 4,994,069 A | 2/1991 | Ritchart et al. | |
| 5,013,318 A | 5/1991 | Spranza, III | |
| 5,040,548 A | 8/1991 | Yock | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,122,154 A | 6/1992 | Rhodes | |
| 5,135,535 A | 8/1992 | Kramer | |
| 5,171,222 A | 12/1992 | Euteneuer et al. | |
| 5,195,984 A | 3/1993 | Schatz | |
| 5,217,495 A | 6/1993 | Kaplan et al. | |
| 5,219,355 A | 6/1993 | Parodi et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,403,341 A | 4/1995 | Solar | |
| 5,421,955 A | 6/1995 | Lau et al. | |
| 5,456,694 A | 10/1995 | Marin et al. | |
| 5,456,713 A | 10/1995 | Chuter | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,591,228 A | 1/1997 | Edoga | |
| 5,593,412 A | 1/1997 | Martinez et al. | |
| 5,607,444 A | 3/1997 | Lam | |
| 5,607,463 A | 3/1997 | Schwartz et al. | |
| 5,609,627 A | 3/1997 | Goicoechea et al. | |
| 5,609,629 A | 3/1997 | Fearnot et al. | |
| 5,628,775 A | 5/1997 | Jackson et al. | |
| 5,632,763 A | 5/1997 | Glastra | |
| 5,632,772 A | 5/1997 | Alcime et al. | |
| 5,634,928 A | 6/1997 | Fischell et al. | |
| 5,639,274 A | 6/1997 | Fischell et al. | |
| 5,662,675 A | 9/1997 | Polanskyj Stockert et al. | |
| 5,669,924 A | 9/1997 | Shaknovich | |
| 5,670,161 A | 9/1997 | Healy et al. | |
| 5,676,654 A | 10/1997 | Ellis et al. | |
| 5,679,400 A | 10/1997 | Tuch | |
| 5,683,451 A | 11/1997 | Lenker et al. | |
| 5,697,948 A | 12/1997 | Marin et al. | |
| 5,697,967 A | 12/1997 | Dinh et al. | |
| 5,702,418 A | 12/1997 | Ravenscroft | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,825 A * | 5/1998 | Fischell | A61F 2/90 |
| | | | 600/3 |
| 5,749,848 A | 5/1998 | Jang et al. | |
| 5,749,921 A | 5/1998 | Lenker et al. | |
| 5,755,734 A * | 5/1998 | Richter | A61F 2/856 |
| | | | 606/194 |
| 5,755,735 A | 5/1998 | Richter et al. | |
| 5,755,771 A | 5/1998 | Penn et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,797,951 A | 8/1998 | Mueller | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,824,048 A | 10/1998 | Tuch | |
| 5,827,320 A | 10/1998 | Richter et al. | |
| 5,833,694 A | 11/1998 | Poncet | |
| 5,836,964 A | 11/1998 | Richter et al. | |
| 5,837,008 A | 11/1998 | Berg et al. | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,893,887 A | 4/1999 | Jayaraman | |
| 5,895,398 A | 4/1999 | Wensel et al. | |
| 5,899,935 A | 5/1999 | Ding | |
| 5,902,332 A | 5/1999 | Schatz | |
| 5,911,754 A | 6/1999 | Kanesaka et al. | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,972,017 A * | 10/1999 | Berg | A61F 2/06 |
| | | | 128/898 |
| 5,972,027 A | 10/1999 | Johnson | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,997,563 A | 12/1999 | Kretzers | |
| 6,004,328 A | 12/1999 | Solar | |
| 6,007,517 A | 12/1999 | Anderson | |
| 6,017,363 A | 1/2000 | Hojeibane | |
| 6,022,359 A | 2/2000 | Frantzen | |
| 6,022,374 A | 2/2000 | Imran | |
| 6,033,434 A | 3/2000 | Borghi | |
| 6,036,725 A | 3/2000 | Avellanet | |
| 6,039,721 A | 3/2000 | Johnson et al. | |

(56) References Cited

U.S. PATENT DOCUMENTS

| | | | |
|---|---|---|---|
| 6,042,589 A | 3/2000 | Marianne | |
| 6,048,361 A * | 4/2000 | Von Oepen | A61F 2/856 |
| | | | 606/108 |
| 6,056,722 A | 5/2000 | Jayaraman | |
| 6,056,775 A | 5/2000 | Borghi et al. | |
| 6,059,811 A | 5/2000 | Pinchasik et al. | |
| 6,059,824 A | 5/2000 | Taheri | |
| 6,066,155 A | 5/2000 | Amann et al. | |
| 6,068,655 A * | 5/2000 | Seguin | A61F 2/07 |
| | | | 623/1.35 |
| 6,070,589 A | 6/2000 | Keith et al. | |
| 6,086,604 A | 7/2000 | Fischell et al. | |
| 6,090,063 A | 7/2000 | Makower et al. | |
| 6,090,136 A | 7/2000 | McDonald et al. | |
| 6,096,071 A | 8/2000 | Yadav | |
| 6,096,073 A * | 8/2000 | Webster | A61F 2/91 |
| | | | 623/1.16 |
| 6,099,497 A | 8/2000 | Adams et al. | |
| 6,102,942 A | 8/2000 | Ahari | |
| 6,106,530 A | 8/2000 | Harada | |
| RE36,857 E | 9/2000 | Euteneuer et al. | |
| 6,117,117 A * | 9/2000 | Mauch | A61F 2/954 |
| | | | 604/103 |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,738 A * | 10/2000 | Lashinski | A61F 2/954 |
| | | | 604/101.04 |
| 6,129,756 A | 10/2000 | Kugler et al. | |
| 6,132,460 A | 10/2000 | Thompson | |
| 6,136,011 A | 10/2000 | Stambaugh | |
| 6,142,973 A | 11/2000 | Carleton et al. | |
| 6,143,016 A | 11/2000 | Bleam et al. | |
| 6,165,167 A | 12/2000 | Delaloye | |
| 6,165,210 A | 12/2000 | Lau et al. | |
| 6,179,878 B1 | 1/2001 | Duerig et al. | |
| 6,183,509 B1 | 2/2001 | Dibie | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,210,429 B1 | 4/2001 | Vardi et al. | |
| 6,221,090 B1 * | 4/2001 | Wilson | A61F 2/856 |
| | | | 606/194 |
| 6,231,600 B1 | 5/2001 | Zhong | |
| 6,238,991 B1 | 5/2001 | Suzuki | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,258,121 B1 | 7/2001 | Yang et al. | |
| 6,264,682 B1 | 7/2001 | Wilson et al. | |
| 6,264,688 B1 | 7/2001 | Herklotz et al. | |
| 6,267,783 B1 | 7/2001 | Letendre et al. | |
| 6,273,895 B1 | 8/2001 | Pinchuk et al. | |
| 6,273,911 B1 | 8/2001 | Cox et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,322,586 B1 | 11/2001 | Monroe et al. | |
| 6,325,823 B1 | 12/2001 | Horzewski et al. | |
| 6,325,826 B1 | 12/2001 | Vardi et al. | |
| 6,326,826 B1 | 12/2001 | Lee et al. | |
| 6,334,871 B1 | 1/2002 | Dor et al. | |
| 6,344,053 B1 | 2/2002 | Boneau | |
| 6,344,056 B1 | 2/2002 | Dehdashtian | |
| 6,344,272 B1 | 2/2002 | Oldenburg et al. | |
| 6,357,104 B1 | 3/2002 | Myers | |
| 6,361,555 B1 | 3/2002 | Wilson | |
| 6,375,676 B1 | 4/2002 | Cox | |
| 6,379,365 B1 | 4/2002 | Diaz | |
| 6,383,171 B1 | 5/2002 | Gifford et al. | |
| 6,383,215 B1 | 5/2002 | Sass | |
| 6,398,807 B1 | 6/2002 | Chouinard et al. | |
| 6,409,753 B1 | 6/2002 | Brown et al. | |
| 6,415,696 B1 | 7/2002 | Erickson et al. | |
| 6,419,693 B1 | 7/2002 | Fariabi | |
| 6,428,811 B1 | 8/2002 | West et al. | |
| 6,443,982 B1 | 9/2002 | Israel et al. | |
| 6,451,025 B1 | 9/2002 | Jervis | |
| 6,451,050 B1 | 9/2002 | Rudakov et al. | |
| 6,464,720 B2 | 10/2002 | Boatman et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,485,511 B2 | 11/2002 | Lau et al. | |
| 6,488,694 B1 | 12/2002 | Lau et al. | |
| 6,488,702 B1 | 12/2002 | Besselink | |
| 6,488,703 B1 | 12/2002 | Kveen et al. | |
| 6,511,468 B1 | 1/2003 | Cragg et al. | |
| 6,514,281 B1 | 2/2003 | Blaeser et al. | |
| 6,520,986 B2 | 2/2003 | Martin et al. | |
| 6,520,987 B1 | 2/2003 | Plante | |
| 6,520,988 B1 * | 2/2003 | Colombo | A61F 2/856 |
| | | | 623/1.11 |
| 6,527,789 B1 | 3/2003 | Lau et al. | |
| 6,527,799 B2 | 3/2003 | Shanley | |
| 6,529,549 B1 | 3/2003 | Norrell et al. | |
| 6,530,944 B2 | 3/2003 | West et al. | |
| 6,540,777 B2 | 4/2003 | Stenzel | |
| 6,540,779 B2 * | 4/2003 | Richter | A61F 2/07 |
| | | | 623/1.35 |
| 6,551,350 B1 | 4/2003 | Thornton et al. | |
| 6,555,157 B1 | 4/2003 | Hossainy | |
| 6,569,180 B1 | 5/2003 | Sirhan et al. | |
| 6,575,993 B1 | 6/2003 | Yock | |
| 6,579,305 B1 | 6/2003 | Lashinski | |
| 6,579,309 B1 | 6/2003 | Loos et al. | |
| 6,582,394 B1 | 6/2003 | Reiss et al. | |
| 6,582,460 B1 | 6/2003 | Cryer | |
| 6,585,756 B1 | 7/2003 | Strecker | |
| 6,592,549 B2 | 7/2003 | Gerdts et al. | |
| 6,592,568 B2 | 7/2003 | Campbell | |
| 6,596,020 B2 | 7/2003 | Vardi et al. | |
| 6,596,022 B2 | 7/2003 | Lau et al. | |
| 6,599,296 B1 | 7/2003 | Gillick et al. | |
| 6,599,314 B2 | 7/2003 | Mathis | |
| 6,602,282 B1 | 8/2003 | Yan | |
| 6,605,062 B1 | 8/2003 | Hurley et al. | |
| 6,605,109 B2 | 8/2003 | Fiedler | |
| 6,607,553 B1 | 8/2003 | Healy et al. | |
| 6,645,517 B2 | 11/2003 | West et al. | |
| 6,645,547 B1 | 11/2003 | Shekalim et al. | |
| 6,656,212 B2 | 12/2003 | Ravenscroft et al. | |
| 6,660,031 B2 | 12/2003 | Tran et al. | |
| 6,660,381 B2 | 12/2003 | Halas et al. | |
| 6,666,883 B1 | 12/2003 | Seguin et al. | |
| 6,676,695 B2 | 1/2004 | Solem et al. | |
| 6,679,909 B2 | 1/2004 | McIntosh et al. | |
| 6,685,721 B1 | 2/2004 | Kramer | |
| 6,685,730 B2 | 2/2004 | West et al. | |
| 6,689,156 B1 | 2/2004 | Davidson et al. | |
| 6,692,465 B2 | 2/2004 | Kramer | |
| 6,692,483 B2 | 2/2004 | Vardi et al. | |
| 6,699,280 B2 | 3/2004 | Camrud et al. | |
| 6,699,724 B1 | 3/2004 | West et al. | |
| 6,702,843 B1 | 3/2004 | Brown et al. | |
| 6,706,062 B2 | 3/2004 | Vardi et al. | |
| 6,709,379 B1 | 3/2004 | Brandau et al. | |
| 6,709,440 B2 | 3/2004 | Callol et al. | |
| 6,712,827 B2 | 3/2004 | Ellis et al. | |
| 6,712,845 B2 | 3/2004 | Hossainy | |
| 6,723,071 B2 | 4/2004 | Gerdts et al. | |
| 6,736,842 B2 | 5/2004 | Healy et al. | |
| 6,743,251 B1 | 6/2004 | Eder | |
| 6,749,628 B1 | 6/2004 | Callol et al. | |
| 6,761,734 B2 | 7/2004 | Suhr | |
| 6,770,091 B2 | 8/2004 | Richter et al. | |
| 6,778,316 B2 | 8/2004 | Halas et al. | |

(56) References Cited

U.S. PATENT DOCUMENTS

| | | |
|---|---|---|
| 6,800,065 B2 | 10/2004 | Duane et al. |
| 6,811,566 B1 | 11/2004 | Penn et al. |
| 6,825,203 B2 | 11/2004 | Pasternak et al. |
| 6,835,203 B1 | 12/2004 | Vardi et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,875,228 B2 | 4/2005 | Pinchasik et al. |
| 6,878,161 B2 | 4/2005 | Lenker |
| 6,879,370 B2 | 4/2005 | Yokoue et al. |
| 6,884,258 B2 | 4/2005 | Vardi et al. |
| 6,893,417 B2 | 5/2005 | Gribbons et al. |
| 6,896,695 B2 | 5/2005 | Mueller et al. |
| 6,908,477 B2 | 6/2005 | McGuckin et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,949,120 B2 | 9/2005 | Kveen et al. |
| 6,951,053 B2 | 10/2005 | Padilla et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,026 B2 | 1/2006 | Richter et al. |
| 7,005,454 B2 | 2/2006 | Brocchini et al. |
| 7,037,327 B2 | 5/2006 | Salmon et al. |
| 7,052,510 B1 | 5/2006 | Richter |
| 7,090,694 B1 | 8/2006 | Morris et al. |
| 7,101,840 B2 | 9/2006 | Brocchini et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,182,779 B2 | 2/2007 | Acosta et al. |
| 7,192,440 B2 | 3/2007 | Andreas et al. |
| 7,220,275 B2 | 5/2007 | Davidson et al. |
| 7,225,518 B2 * | 6/2007 | Eidenschink ........... A61F 2/954 29/283.5 |
| 7,241,308 B2 | 7/2007 | Andreas et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,323,009 B2 | 1/2008 | Suhr et al. |
| 7,326,236 B2 | 2/2008 | Andreas et al. |
| 7,326,242 B2 | 2/2008 | Eidenschink |
| 7,341,598 B2 | 3/2008 | Davidson et al. |
| 7,344,556 B2 | 3/2008 | Sequin et al. |
| 7,387,639 B2 | 6/2008 | Bourang et al. |
| 7,445,688 B2 | 11/2008 | Suzuki et al. |
| 7,520,895 B2 | 4/2009 | Douglas et al. |
| 7,537,609 B2 | 5/2009 | Davidson et al. |
| 7,540,881 B2 | 6/2009 | Meyer et al. |
| 7,635,383 B2 | 12/2009 | Gumm |
| 7,641,684 B2 | 1/2010 | Hilaire et al. |
| 7,641,685 B2 | 1/2010 | Richter |
| 7,686,846 B2 * | 3/2010 | Laborde ................ A61F 2/954 623/1.35 |
| 7,695,508 B2 * | 4/2010 | Der Leest ............... A61F 2/856 623/1.35 |
| 7,799,064 B2 * | 9/2010 | Brucker ................ A61F 2/954 623/1.11 |
| 8,016,870 B2 | 9/2011 | Chew et al. |
| 8,070,789 B2 | 12/2011 | Will et al. |
| 8,206,429 B2 * | 6/2012 | Gregorich ......... A61M 25/1027 623/1.11 |
| 8,769,796 B2 | 7/2014 | Bourang et al. |
| 8,795,347 B2 | 8/2014 | Bourang et al. |
| 8,808,347 B2 | 8/2014 | Bourang et al. |
| 8,821,562 B2 | 9/2014 | Bourang et al. |
| 8,828,071 B2 | 9/2014 | Bourang et al. |
| 8,979,917 B2 | 3/2015 | Bourang et al. |
| 9,254,210 B2 | 2/2016 | Bourang |
| 9,364,356 B2 | 6/2016 | Bourang |
| 9,724,218 B2 | 8/2017 | Bourang et al. |
| 9,730,821 B2 | 8/2017 | Bourang et al. |
| 9,737,424 B2 | 8/2017 | Bourang et al. |
| 9,855,158 B2 | 1/2018 | Bourang et al. |
| 10,219,926 B2 | 3/2019 | Bourang et al. |
| 10,219,927 B2 | 3/2019 | Bourang et al. |
| 10,610,391 B2 | 4/2020 | Bourang et al. |
| 2001/0003161 A1 | 6/2001 | Vardi et al. |
| 2001/0020154 A1 | 9/2001 | Bigus et al. |
| 2001/0020181 A1 | 9/2001 | Layne |
| 2001/0039395 A1 | 11/2001 | Mareiro et al. |
| 2001/0044595 A1 | 11/2001 | Reydel et al. |
| 2001/0044622 A1 | 11/2001 | Vardi et al. |
| 2001/0044632 A1 | 11/2001 | Daniel et al. |
| 2001/0049547 A1 | 12/2001 | Moore |
| 2002/0037358 A1 | 3/2002 | Barry et al. |
| 2002/0091439 A1 | 7/2002 | Baker et al. |
| 2002/0107560 A1 | 8/2002 | Richter |
| 2002/0111671 A1 | 8/2002 | Stenzel |
| 2002/0128706 A1 | 9/2002 | Osypka |
| 2002/0138132 A1 | 9/2002 | Brown |
| 2002/0143382 A1 | 10/2002 | Hijlkema et al. |
| 2002/0151924 A1 | 10/2002 | Shiber |
| 2002/0151955 A1 | 10/2002 | Tran et al. |
| 2002/0156496 A1 | 10/2002 | Chermoni |
| 2002/0173835 A1 | 11/2002 | Bourang et al. |
| 2002/0177890 A1 | 11/2002 | Lenker |
| 2002/0183763 A1 * | 12/2002 | Callol ..................... A61F 2/856 606/108 |
| 2002/0188343 A1 | 12/2002 | Mathis |
| 2002/0188347 A1 | 12/2002 | Mathis |
| 2002/0193873 A1 | 12/2002 | Brucker et al. |
| 2003/0028233 A1 | 2/2003 | Vardi et al. |
| 2003/0029039 A1 | 2/2003 | Richter et al. |
| 2003/0045923 A1 | 3/2003 | Bashiri |
| 2003/0093143 A1 | 5/2003 | Zhao et al. |
| 2003/0097169 A1 | 5/2003 | Brucker et al. |
| 2003/0105922 A1 | 6/2003 | Tomita |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0192164 A1 | 10/2003 | Austin |
| 2003/0195609 A1 | 10/2003 | Berenstein et al. |
| 2003/0199821 A1 | 10/2003 | Gerdts et al. |
| 2003/0204238 A1 | 10/2003 | Tedeschi |
| 2003/0212447 A1 | 11/2003 | Euteneuer et al. |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0044398 A1 | 3/2004 | Nicholas |
| 2004/0085845 A1 | 5/2004 | Ooishi |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea et al. |
| 2004/0111145 A1 | 6/2004 | Serino et al. |
| 2004/0117008 A1 | 6/2004 | Wnendt et al. |
| 2004/0176832 A1 | 9/2004 | Hartley et al. |
| 2004/0186551 A1 | 9/2004 | Kao et al. |
| 2004/0193245 A1 | 9/2004 | Deem et al. |
| 2004/0215165 A1 | 10/2004 | Coyle et al. |

(56) References Cited

U.S. PATENT DOCUMENTS

| | | |
|---|---|---|
| 2004/0215312 A1 | 10/2004 | Andreas |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2005/0010276 A1 | 1/2005 | Acosta et al. |
| 2005/0038505 A1 | 2/2005 | Shulze et al. |
| 2005/0049673 A1 | 3/2005 | Andreas et al. |
| 2005/0049680 A1 | 3/2005 | Fischell et al. |
| 2005/0080474 A1 | 4/2005 | Andreas et al. |
| 2005/0080475 A1 | 4/2005 | Andreas et al. |
| 2005/0085845 A1 | 4/2005 | Hilaire et al. |
| 2005/0090846 A1 | 4/2005 | Pedersen et al. |
| 2005/0101624 A1 | 5/2005 | Betts et al. |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0143827 A1 | 6/2005 | Globerman et al. |
| 2005/0149159 A1 | 7/2005 | Andreas et al. |
| 2005/0165378 A1 | 7/2005 | Heinrich et al. |
| 2005/0182473 A1 | 8/2005 | Eidenschink et al. |
| 2005/0183259 A1* | 8/2005 | Eidenschink ........ A61F 2/954 29/508 |
| 2005/0197688 A1 | 9/2005 | Theron et al. |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0245941 A1 | 11/2005 | Vardi et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0100694 A1* | 5/2006 | Globerman ............ A61F 2/856 623/1.35 |
| 2006/0116748 A1 | 6/2006 | Kaplan et al. |
| 2006/0123874 A1 | 6/2006 | Motsenbocker |
| 2006/0155362 A1 | 7/2006 | Israel |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271090 A1 | 11/2006 | Shaked et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0027521 A1 | 2/2007 | Andreas et al. |
| 2007/0027524 A1 | 2/2007 | Johnson et al. |
| 2007/0055351 A1 | 3/2007 | Eidenschink et al. |
| 2007/0061003 A1 | 3/2007 | Shmulewitz et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0123970 A1 | 5/2007 | Lenz |
| 2007/0129733 A1 | 6/2007 | Will et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0203571 A1 | 8/2007 | Kaplan et al. |
| 2007/0219611 A1 | 9/2007 | Krever et al. |
| 2007/0219612 A1 | 9/2007 | Andreas et al. |
| 2007/0219613 A1 | 9/2007 | Kao et al. |
| 2007/0219625 A1 | 9/2007 | Venturelli et al. |
| 2007/0264305 A1 | 11/2007 | Von Oepen et al. |
| 2007/0265637 A1 | 11/2007 | Andreas et al. |
| 2007/0270936 A1 | 11/2007 | Andreas et al. |
| 2007/0276460 A1 | 11/2007 | Davis et al. |
| 2007/0276461 A1 | 11/2007 | Andreas et al. |
| 2007/0281117 A1 | 12/2007 | Kaplan et al. |
| 2007/0282419 A1 | 12/2007 | Hilaire et al. |
| 2007/0292518 A1 | 12/2007 | Ludwig |
| 2008/0009932 A1 | 1/2008 | Ta et al. |
| 2008/0009933 A1 | 1/2008 | Ta et al. |
| 2008/0051869 A1 | 2/2008 | Yribarren |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0132989 A1 | 6/2008 | Snow et al. |
| 2008/0147162 A1 | 6/2008 | Andreas et al. |
| 2008/0199510 A1 | 8/2008 | Ruane et al. |
| 2008/0208309 A1 | 8/2008 | Saeed |
| 2008/0208311 A1 | 8/2008 | Kao et al. |
| 2008/0208318 A1 | 8/2008 | Kao et al. |
| 2008/0221655 A1 | 9/2008 | Miller |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0269865 A1 | 10/2008 | Snow et al. |
| 2009/0048655 A1* | 2/2009 | Jang ................ A61F 2/958 623/1.11 |
| 2009/0076584 A1 | 3/2009 | Mao et al. |
| 2009/0105686 A1 | 4/2009 | Snow et al. |
| 2009/0132019 A1 | 5/2009 | Duffy et al. |
| 2009/0143854 A1 | 6/2009 | Adams et al. |
| 2009/0171430 A1 | 7/2009 | Baim et al. |
| 2009/0182270 A1 | 7/2009 | Nanavati |
| 2009/0182409 A1 | 7/2009 | Feld et al. |
| 2009/0228088 A1 | 9/2009 | Lowe et al. |
| 2009/0240321 A1 | 9/2009 | Davidson et al. |
| 2009/0254167 A1 | 10/2009 | Ricci et al. |
| 2009/0259285 A1 | 10/2009 | Duane et al. |
| 2009/0287289 A1* | 11/2009 | Sagedahl ............ A61F 2/856 623/1.11 |
| 2009/0299454 A1 | 12/2009 | Jennings et al. |
| 2009/0319030 A1 | 12/2009 | Yadin et al. |
| 2009/0326641 A1 | 12/2009 | Davis et al. |
| 2010/0004737 A1 | 1/2010 | Eidenschink |
| 2010/0030183 A1 | 2/2010 | Toner et al. |
| 2010/0036477 A1 | 2/2010 | Bronson et al. |
| 2010/0042199 A1 | 2/2010 | Burton |
| 2010/0049298 A1 | 2/2010 | Hamer et al. |
| 2010/0057020 A1 | 3/2010 | Uretsky |
| 2010/0063571 A1 | 3/2010 | Roach et al. |
| 2010/0106238 A1 | 4/2010 | Hilaire et al. |
| 2010/0222861 A1 | 9/2010 | Dibie |
| 2011/0029061 A1 | 2/2011 | Ahn et al. |
| 2011/0282427 A1 | 11/2011 | Bourang et al. |
| 2011/0307044 A1 | 12/2011 | Bourang et al. |
| 2011/0307045 A1 | 12/2011 | Bourang et al. |
| 2011/0307046 A1 | 12/2011 | Bourang et al. |
| 2011/0307047 A1 | 12/2011 | Bourang et al. |
| 2011/0307052 A1 | 12/2011 | Bourang et al. |
| 2013/0268047 A1 | 10/2013 | Bourang |
| 2014/0100647 A1 | 4/2014 | Bourang |
| 2015/0032196 A1 | 1/2015 | Bourang et al. |
| 2015/0073521 A1 | 3/2015 | Bourang et al. |
| 2015/0073527 A1 | 3/2015 | Bourang et al. |
| 2015/0081001 A1 | 3/2015 | Bourang et al. |
| 2015/0081002 A1 | 3/2015 | Bourang et al. |
| 2015/0216690 A1 | 8/2015 | Bourang et al. |
| 2016/0100966 A1 | 4/2016 | Bourang |
| 2016/0256303 A1 | 9/2016 | Bourang |
| 2018/0085239 A1 | 3/2018 | Bourang et al. |
| 2019/0151126 A1 | 5/2019 | Bourang et al. |
| 2019/0151127 A1 | 5/2019 | Bourang et al. |
| 2020/0188150 A1 | 6/2020 | Bourang et al. |

FOREIGN PATENT DOCUMENTS

| | | |
|---|---|---|
| CN | 1867374 A | 11/2006 |
| CN | 101035488 A | 9/2007 |
| CN | 102215780 A | 10/2011 |
| CN | 103037813 A | 4/2013 |

(56) References Cited

FOREIGN PATENT DOCUMENTS

| | | | |
|---|---|---|---|
| CN | 103037815 A | 4/2013 | |
| CN | 103037816 A | 4/2013 | |
| CN | 103037817 A | 4/2013 | |
| CN | 103068345 A | 4/2013 | |
| EP | 0203945 A1 | 12/1986 | |
| EP | 0274129 A2 | 7/1988 | |
| EP | 0282143 A1 | 9/1988 | |
| EP | 0274129 B1 | 5/1992 | |
| EP | 0505686 A1 | 9/1992 | |
| EP | 0533960 A1 | 3/1993 | |
| EP | 0596145 A1 | 5/1994 | |
| EP | 0714640 A1 | 6/1996 | |
| EP | 0203945 B2 | 6/1998 | |
| EP | 0897700 A1 | 2/1999 | |
| EP | 0947180 A2 | 10/1999 | |
| EP | 1074227 A2 | 2/2001 | |
| EP | 1258230 A2 | 11/2002 | |
| EP | 1266638 A2 | 12/2002 | |
| EP | 1277449 A1 | 1/2003 | |
| EP | 1523959 A2 | 4/2005 | |
| EP | 1523960 A2 | 4/2005 | |
| EP | 1266638 B1 | 10/2005 | |
| EP | 1788977 A1 | 5/2007 | |
| EP | 1867374 A1 | 12/2007 | |
| EP | 1788977 B1 | 3/2008 | |
| EP | 1905398 A2 | 4/2008 | |
| EP | 2036519 A1 | 3/2009 | |
| EP | 2344068 A1 | 7/2011 | |
| EP | 2549949 A1 | 1/2013 | |
| EP | 2549950 A1 | 1/2013 | |
| EP | 2549951 A1 | 1/2013 | |
| EP | 2549952 A1 | 1/2013 | |
| EP | 2549958 A1 | 1/2013 | |
| EP | 2672925 A2 | 12/2013 | |
| EP | 2672932 A1 | 12/2013 | |
| EP | 2549951 B1 | 5/2017 | |
| FR | 2733689 A1 | 11/1996 | |
| JP | H1043313 A | 2/1998 | |
| JP | 2003532437 A | 11/2003 | |
| JP | 2004052887 A | 2/2004 | |
| JP | 2004528877 A | 9/2004 | |
| JP | 2007508082 A | 4/2007 | |
| JP | 2010503465 A | 2/2010 | |
| JP | 2012503534 A | 2/2012 | |
| JP | 2013523215 A | 6/2013 | |
| WO | WO-9013332 A1 | 11/1990 | |
| WO | WO-9112779 A1 | 9/1991 | |
| WO | WO-9626689 A1 | 9/1996 | |
| WO | WO-9633677 A1 | 10/1996 | |
| WO | WO-9746174 A1 | 12/1997 | |
| WO | WO-9748351 A1 | 12/1997 | |
| WO | WO-9820810 A1 | 5/1998 | |
| WO | WO-9837833 A1 | 9/1998 | |
| WO | WO-9858600 A1 | 12/1998 | |
| WO | WO-9901087 A1 | 1/1999 | |
| WO | WO-0012832 A2 | 3/2000 | |
| WO | WO-0015151 A1 | 3/2000 | |
| WO | WO-0025841 A1 | 5/2000 | |
| WO | WO-0012832 A3 | 6/2000 | |
| WO | WO-0032136 A1 | 6/2000 | |
| WO | WO-0041649 A1 | 7/2000 | |
| WO | WO-0050116 A1 | 8/2000 | |
| WO | WO-0062708 A1 | 10/2000 | |
| WO | WO-0072780 A1 | 12/2000 | |
| WO | WO-0074595 A1 | 12/2000 | |
| WO | WO-0170297 A2 | 9/2001 | |
| WO | WO-0191918 A1 | 12/2001 | |
| WO | WO-02060344 A2 | 8/2002 | |
| WO | WO-02085253 A1 | 10/2002 | |
| WO | WO-03022178 A1 | 3/2003 | |
| WO | WO-03047651 A2 | 6/2003 | |
| WO | WO-03051425 A2 | 6/2003 | |
| WO | WO-03055414 A1 | 7/2003 | |
| WO | WO-03105922 A2 | 12/2003 | |
| WO | WO-2004017865 A1 | 3/2004 | |
| WO | WO-2004043299 A1 | 5/2004 | |
| WO | WO-2004043301 A1 | 5/2004 | |
| WO | WO-2004043510 A1 | 5/2004 | |
| WO | WO-2004052237 A2 | 6/2004 | |
| WO | WO-2005013853 A2 | 2/2005 | |
| WO | WO-2005039681 A1 | 5/2005 | |
| WO | WO-2006036939 A2 | 4/2006 | |
| WO | WO-2006047520 A2 | 5/2006 | |
| WO | WO-2007035805 A2 | 3/2007 | |
| WO | WO-2007053187 A2 | 5/2007 | |
| WO | WO-2007146411 A2 | 12/2007 | |
| WO | WO-2008005111 A1 | 1/2008 | |
| WO | WO-2008033621 A1 | 3/2008 | |
| WO | WO-2008130503 A2 | 10/2008 | |
| WO | WO-2009148594 A1 | 12/2009 | |
| WO | WO-2009148997 A1 | 12/2009 | |
| WO | WO-2010022516 A1 | 3/2010 | |
| WO | WO-2010036982 A1 | 4/2010 | |
| WO | WO-2011119879 A1 | 9/2011 | |
| WO | WO-2011119880 A1 | 9/2011 | |
| WO | WO-2011119882 A1 | 9/2011 | |
| WO | WO-2011119883 A1 | 9/2011 | |
| WO | WO-2011119884 A1 | 9/2011 | |
| WO | WO-2012109365 A1 | 8/2012 | |
| WO | WO-2012109382 A2 | 8/2012 | |
| WO | WO-2012109382 A3 | 1/2013 | |

OTHER PUBLICATIONS

Cooley, Patrick et al. "Applications of Ink-Jet Printing Technology to BioMEMs and Microfluidic Systems"; Proceedings, SPIE Conference on Microfluidics and BioMEMs; Oct. 2001; 12 pages.
Drug Delivery Stent With Holes Located on Neutral Axis; No. 429007; Research Disclosure, Kenneth Mason Publications, Hampshire, CB; vol. 2266, Jan. 2000; pp. 13.
English Translation and Notice of the Third Office Action for corresponding Chinese Patent Application No. 2009801473592.X dated Nov. 24, 2014, 16 pages.
English Translation and Second Office Action for corresponding Chinese Patent Application No. 200980143592.X dated Apr. 21, 2014, 26 pages.
Evans Analytical Group; "Functional Sites on Non-polymeric Materials: Gas Plasma Treatment and Surface Analysis"; located at http://www.eaglabs.com;2003; 2 pages.
First Office Action for corresponding Chinese Application No. 200980143592.X dated Jun. 4, 2013, 10 pages.
International Preliminary Report on Patentability of Application No. PCT/US2009/058505, dated Oct. 28, 2010, 38 pages.
International Preliminary Report on Patentability of Application No. PCT/US2011/029859, dated Sep. 25, 2012, 8 pages.
International Preliminary Report on Patentability of Application No. PCT/US2011/029861, dated Oct. Sep. 25, 2012, 9 pages.
International Preliminary Report on Patentability of Application No. PCT/US2011/029862, dated Sep. 25, 2012, 11 pages.
International Preliminary Report on Patentability of Application No. PCT/US2011/029863, dated Sep. 25, 2012, 13 pages.
International Preliminary Report on Patentability of Application No. PCT/US2012/024347, dated Aug. 13, 2013, 8 pages.
International Preliminary Report on Patentability of Application No. PCT/US2012/024366, dated Aug. 13, 2013, 19 pages.
International Search Report and Written Opinion of Application No. PCT/US2009/058505, dated Nov. 25, 2009, 11 pages.
International Search Report and Written Opinion of Application No. PCT/US2011/029858, dated May 25, 2011, 10 pages.
International Search Report and Written Opinion of Application No. PCT/US2011/029859, dated May 23, 2011, 8 pages.
International Search Report and Written Opinion of Application No. PCT/US2011/029861, dated May 20, 2011, 11 pages.
International Search Report and Written Opinion of Application No. PCT/US2011/029862, dated May 25, 2011, 13 pages.
International Search Report and Written Opinion of Application No. PCT/US2012/024347, dated Jun. 29, 2012, 13 pages.
International Search Report and Written Opinion of Application No. PCT/US2012/024366, dated Sep. 7, 2012, 23 pages.

(56) References Cited

OTHER PUBLICATIONS

International Search Report for PCT Patent Application No. PCT/US2011/029863, dated May 27, 2011, 2011, 2 pages.
Invitation to Pay Additional Fees of Application No. PCT/US2012/024366, dated Jun. 1, 2012, 3 pages.
Joung, "Estrogen release from metallic stent surface for the prevention of restenosis", Journal of Controlled Release, vol. 92, 2003, pp. 83-91.
Lefevre, Thierry et al. "Approach to Coronary Bifurcation Stenting in 2003"; Euro PCR; May 2003; pp. 127-154.
Notice of Allowance dated Mar. 26, 2014 for U.S. Appl. No. 13/071,149.
Office Action for corresponding Japanese Patent Application No. 2011-529290, dated Sep. 25, 2013, 5 pages.
Stent. Definitions from Dictionary. com. Unabridged (v1.01 ). Retrieved Sep. 22, 2006, from Dictionary.com, located at http://dictionary.reference.com/search?q=stent; 1 page.
Stimpson, Donald I. et al; "Parallel Production of Oligonucleotide Arrays Using Membranes and Reagent Jet Printing"; BioTechniques; vol. 25, Nov. 1998; pp. 886-890.
Supplementary European Search Report dated Apr. 9, 2008, for EP Patent Application No. 05744136.2, 3 pages.
Supplementary European Search Report dated Mar. 25, 2008, for EP Patent Application No. 05727731.1, 2 pages.
U.S. Appl. No. 60/561,041, filed Apr. 9, 2004 by Jeffry Grainger et al.
U.S. Appl. No. 09/097,855, filed Jun. 15, 1998 by Enrique J. Klein et al.
U.S. Appl. No. 09/225,364, filed Jan. 4, 1999 by Aaron V. Kaplan et al.
U.S. Appl. No. 10/874,859, filed Jun. 22, 2004 by Pablo Acosta et al.
U.S. Appl. No. 60/336,607, filed Dec. 3, 2001 by Bernard Andreas et al.
U.S. Appl. No. 60/336,767, filed Dec. 3, 2001 by Bernard Andreas et al.
U.S. Appl. No. 60/336,967, filed Dec. 3, 2001 by Sunmi Chew et al.
U.S. Appl. No. 60/364,389, filed Mar. 13, 2002 by Sunmi Chew et al.
U.S. Appl. No. 60/440,839, filed Jan. 17, 2003 by Bernard Andreas et al.
U.S. Appl. No. 60/784,309, filed Mar. 20, 2006 by Bernard Andreas et al.
U.S. Appl. No. 60/810,522, filed Jun. 2, 2006 by Stephen Kaplan et al.
U.S. Appl. No. 60/890,703, filed Feb. 20, 2007 by Patrick Ruane et al.
U.S. Appl. No. 61/012,317, filed Dec. 7, 2007 by Patrick Ruane et al.
Written Opinion of the International Searching Authority for PCT Patent Application No. PCT/US2011/029863, dated May 27, 2011, 11 pages.
"U.S. Appl. No. 15/831,110, Non Final Office Action dated Oct. 18, 2019", 18 pgs.
"U.S. Appl. No. 13/071,149, 312 Amendment filed May 29, 2014", 3 pgs.
"U.S. Appl. No. 13/071,149, PTO Response to Rule 312 Communication dated Jul. 14, 2014", 2 pgs.
"U.S. Appl. No. 13/071,149, Response filed Feb. 3, 2014 to Final Office Action dated Nov. 5, 2013", 9 pgs.
"U.S. Appl. No. 13/071,149, Response filed Feb. 26, 2013 to Restriction Requirement dated Jan. 30, 2013", 2 pgs.
"U.S. Appl. No. 13/071,149, Response filed Oct. 3, 2013 to Non Final Office Action dated Apr. 11, 2013", 16 pgs.
"U.S. Appl. No. 13/071,149, Restriction Requirement dated Jan. 30, 2013", 7 pgs.
"U.S. Appl. No. 13/071,162, 312 Amendment filed May 29, 2014", 3 pgs.
"U.S. Appl. No. 13/071,162, 312 Amendment filed Aug. 7, 2014", 3 pgs.
"U.S. Appl. No. 13/071,162, Examiner Interview Summary dated Feb. 6, 2014", 3 pgs.
"U.S. Appl. No. 13/071,162, PTO Response to Rule 312 Communication dated Jul. 22, 2014", 3 pgs.
"U.S. Appl. No. 13/071,162, PTO Response to Rule 312 Communication dated Aug. 12, 2014", 2 pgs.
"U.S. Appl. No. 13/071,162, Response filed Jan. 30, 2014 to Non Final Office Action dated Aug. 30, 2013", 12 pgs.
"U.S. Appl. No. 13/071,162, Response filed Jul. 11, 2013 to Restriction Requirement dated Apr. 11, 2013", 1 pg.
"U.S. Appl. No. 13/071,162, Restriction Requirement dated Apr. 11, 2013", 7 pgs.
"U.S. Appl. No. 13/071,183, 312 Amendment filed May 29, 2014", 3 pgs.
"U.S. Appl. No. 13/071,183, Examiner Interview Summary dated Feb. 6, 2014", 3 pgs.
"U.S. Appl. No. 13/071,183, PTO Response to Rule 312 Communication dated Jul. 22, 2014", 3 pgs.
"U.S. Appl. No. 13/071,183, Response filed Feb. 5, 2014 to Final Office Action dated Nov. 5, 2013", 14 pgs.
"U.S. Appl. No. 13/071,183, Response filed Aug. 5, 2013 to Non Final Office Action dated Mar. 29, 2013", 20 pgs.
"U.S. Appl. No. 13/071,183, Response filed Oct. 15, 2012 to Restriction Requirement dated Sep. 13, 2012", 1 pg.
"U.S. Appl. No. 13/071,183, Restriction Requirement dated Sep. 13, 2012", 7 pgs.
"U.S. Appl. No. 13/071,198, 312 Amendment filed May 29, 2014", 7 pgs.
"U.S. Appl. No. 13/071,198, 312 Amendment filed Jun. 24, 2014", 3 pgs.
"U.S. Appl. No. 13/071,198, Examiner Interview Summary dated Feb. 5, 2014", 3 pgs.
"U.S. Appl. No. 13/071,198, PTO Response to Rule 312 Communication dated Jun. 27, 2014", 2 pgs.
"U.S. Appl. No. 13/071,198, PTO Response to Rule 312 Communication dated Jul. 3, 2014", 3 pgs.
"U.S. Appl. No. 13/071,198, Response filed Feb. 6, 2014 to Final Office Action dated Nov. 6, 2013", 10 pgs.
"U.S. Appl. No. 13/071,198, Response filed Oct. 10, 2013 to Non Final Office Action dated Apr. 11, 2013", 11 pgs.
"U.S. Appl. No. 13/071,198, Response filed Nov. 12, 2012 to Restriction Requirement dated Oct. 16, 2012", 2 pgs.
"U.S. Appl. No. 13/071,198, Restriction Requirement dated Oct. 16, 2012", 7 pgs.
"U.S. Appl. No. 13/071,239, Examiner Interview Summary dated Feb. 5, 2014", 4 pgs.
"U.S. Appl. No. 13/071,239, PTO Response to 312 Communication dated Jun. 9, 2014", 2 pgs.
"U.S. Appl. No. 13/071,239, Response filed Feb. 6, 2014 to Final Office Action dated Nov. 26, 2013", 8 pgs.
"U.S. Appl. No. 13/071,239, Response filed Sep. 16, 2013 to Non Final Office Action dated Mar. 14, 2013", 9 pgs.
"U.S. Appl. No. 13/071,239, Response filed Nov. 12, 2012 to Restriction Requirement dated Oct. 12, 2012", 2 pgs.
"U.S. Appl. No. 13/071,239, Restriction Requirement dated Oct. 12, 2012", 8 pgs.
"U.S. Appl. No. 14/294,631, Examiner Interview Summary dated Feb. 8, 2017", 3 pgs.
"U.S. Appl. No. 14/294,631, Examiner Interview Summary dated Apr. 11, 2018", 4 pgs.
"U.S. Appl. No. 14/294,631, Notice of Allowance dated Jul. 17, 2018", 9 pgs.
"U.S. Appl. No. 14/294,631, Response filed Feb. 7, 2017 to Non Final Office Action dated Oct. 7, 2016", 10 pgs.
"U.S. Appl. No. 14/294,631, Response filed Mar. 21, 2018 to Non Final Office Action dated Sep. 22, 2017", 8 pgs.
"U.S. Appl. No. 14/294,631, Response filed Jul. 24, 2017 to Final Office Action dated Mar. 24, 2017", 8 pgs.
"U.S. Appl. No. 14/314,361, Examiner Interview Summary dated Feb. 8, 2017", 3 pgs.
"U.S. Appl. No. 14/314,361, Examiner Interview Summary dated Mar. 24, 2017", 2 pgs.

(56) References Cited

OTHER PUBLICATIONS

"U.S. Appl. No. 14/314,361, Response filed Feb. 6, 2017 to Non Final Office Action dated Oct. 6, 2016", 17 pgs.
"U.S. Appl. No. 14/317,387, Examiner Interview Summary dated Feb. 9, 2017", 3 pgs.
"U.S. Appl. No. 14/317,387, Examiner Interview Summary dated Mar. 24, 2017", 2 pgs.
"U.S. Appl. No. 14/317,387, Response filed Feb. 6, 2017 to Non Final Office Action dated Oct. 6, 2016", 14 pgs.
"U.S. Appl. No. 14/321,506, Examiner Interview Summary dated Feb. 8, 2017", 3 pgs.
"U.S. Appl. No. 14/321,506, Examiner Interview Summary dated Mar. 24, 2017", 2 pgs.
"U.S. Appl. No. 14/321,506, Response filed Feb. 6, 2017 to Non Final Office Action dated Oct. 6, 2016", 12 pgs.
"U.S. Appl. No. 14/621,231, Examiner Interview Summary dated May 8, 2018", 4 pgs.
"U.S. Appl. No. 14/621,231, Notice of Allowance dated Jul. 31, 2018", 11 pgs.
"U.S. Appl. No. 14/621,231, Preliminary Amendment filed Apr. 27, 2015", 3 pgs.
"U.S. Appl. No. 14/621,231, Preliminary Amendment filed May 26, 2015", 6 pgs.
"U.S. Appl. No. 14/621,231, Response filed Apr. 19, 2018 to Final Office Action dated Oct. 20, 2017", 9 pgs.
"U.S. Appl. No. 14/621,231, Response filed May 22, 2017 to Restriction Requirement dated Mar. 21, 2017", 1 pg.
"U.S. Appl. No. 14/621,231, Response filed Sep. 14, 2017 to Non Final Office Action dated Jun. 15, 2017", 9 pgs.
"U.S. Appl. No. 14/621,231, Restriction Requirement dated Mar. 21, 2017", 8 pgs.
"U.S. Appl. No. 14/621,231, Supplemental Amendment filed Jun. 1, 2018", 8 pgs.
"U.S. Appl. No. 15/831,110, Preliminary Amendment filed Apr. 18, 2018", 5 pgs.
"Chinese Application Serial No. 200980143592.X, Final Office Action dated Jun. 4, 2013", 10 pgs.
"International Application Serial No. PCT/US11/29859, International Search Report dated May 23, 2011", 2 pgs.
"International Application Serial No. PCT/US11/29859, Written Opinion dated May 23, 2011", 6 pgs.
"International Application Serial No. PCT/US11/29861, International Search Report dated May 20, 2011", 2 pgs.
"International Application Serial No. PCT/US11/29861, Written Opinion dated May 20, 2011", 7 pgs.
Bourang, et al., "U.S. Appl. No. 14/294,631, filed Jun. 3, 2014", 151 pgs.
Bourang, et al., "U.S. Appl. No. 14/313,742, filed Jun. 24, 2014", 142 pgs.
Bourang, et al., "U.S. Appl. No. 14/314,361, filed Jun. 25, 2014", 132 pgs.
Bourang, et al., "U.S. Appl. No. 14/317,387, filed Jun. 27, 2014", (filed Jun. 27, 2014), 39 pgs.
Bourang, et al., "U.S. Appl. No. 14/321,506, filed Jul. 1, 2014", 131 pgs.
Bourang, et al., "U.S. Appl. No. 14/621,231, filed Feb. 12, 2015", 138 pgs.
Co-pending U.S. Appl. No. 15/831,110, filed Dec. 4, 2017.
Dichek, et al. Seeding of intravascular stents with genetically engineered endothelial cells. Circulation 80, 1347-1353, 1989.
English Translation and Notice of First Office Action for corresponding Chinese Patent Application No. 201180025662.9 dated Aug. 21, 2014, 25 pages.
English Translation and Notice of First Office Action for corresponding Chinese Patent Application No. 201180025670.3 dated Aug. 20, 2014, 24 pages.
English Translation and Notice of First Office Action for corresponding Chinese Patent Application No. 201180025716.1 dated Aug. 22, 2014, 28 pages.
English Translation and Notice of Reasons for Rejection for corresponding Japanese Patent Application No. 2013-501497 dated Nov. 5, 2014, 7 pages.
English Translation and Notice of the First Office Action for corresponding Chinese Patent Application No. 201180025742.4 dated Oct. 29, 2014, 12 pages.
English Translation and Notice of the First Office Action for corresponding Chinese Patent Application No. 201180025746.2 dated Sep. 28, 2014, 21 pages.
Notice of Allowance dated Feb. 16, 2016 for U.S. Appl. No. 13/796,424.
Notice of Allowance dated Mar. 4, 2014 for U.S. Appl. No. 13/071,239.
Notice of Allowance dated Mar. 20, 2014 for U.S. Appl. No. 13/071,183.
Notice of Allowance dated Mar. 24, 2014 for U.S. Appl. No. 13/071,198.
Notice of Allowance dated Mar. 31, 2014 for U.S. Appl. No. 13/071,162.
Notice of Allowance dated Apr. 4, 2017 for U.S. Appl. No. 14/321,506.
Notice of Allowance dated Apr. 12, 2017 for U.S. Appl. No. 14/314,361.
Notice of Allowance dated Apr. 17, 2017 for U.S. Appl. No. 14/317,387.
Notice of Allowance dated Aug. 13, 2014 for U.S. Appl. No. 13/071,251.
Notice of Allowance dated Oct. 7, 2015 for U.S. Appl. No. 13/796,466.
Notice of allowance dated Oct. 20, 2017 for U.S. Appl. No. 14/313,742.
Notice of Allowance dated Nov. 18, 2015 for U.S. Appl. No. 13/796,466.
Notice of Allowance for U.S. Appl. No. 13/071,251 dated May 28, 2014, 13 pages.
Office action dated Jan. 29, 2016 for U.S. Appl. No. 14/313,742.
Office action dated Mar. 14, 2013 for U.S. Appl. No. 13/071,239.
Office action dated Mar. 24, 2017 for U.S. Appl. No. 14/294,631.
Office action dated Mar. 24, 2017 for U.S. Appl. No. 14/313,742.
Office action dated Mar. 29, 2013 for U.S. Appl. No. 13/071,183.
Office action dated Apr. 3, 2015 for U.S. Appl. No. 13/796,466.
Office action dated Apr. 11, 2013 for U.S. Appl. No. 13/071,149.
Office action dated Apr. 11, 2013 for U.S. Appl. No. 13/071,198.
Office action dated Jun. 15, 2017 for U.S. Appl. No. 14/621,231.
Office action dated Aug. 11, 2017 for U.S. Appl. No. 15/157,321.
Office action dated Aug. 12, 2016 for U.S. Appl. No. 14/313,742.
Office action dated Aug. 30, 2013 for U.S. Appl. No. 13/071,162.
Office action dated Sep. 10, 2013 for U.S. Appl. No. 13/071,251.
Office action dated Sep. 22, 2017 for U.S. Appl. No. 14/294,631.
Office action dated Oct. 6, 2016 for U.S. Appl. No. 14/314,361.
Office action dated Oct. 6, 2016 for U.S. Appl. No. 14/317,387.
Office action dated Oct. 6, 2016 for U.S. Appl. No. 14/321,506.
Office action dated Oct. 7, 2016 for U.S. Appl. No. 14/294,631.
Office action dated Oct. 20, 2017 for U.S. Appl. No. 14/621,231.
Office action dated Nov. 5, 2013 for U.S. Appl. No. 13/071,149.
Office action dated Nov. 5, 2013 for U.S. Appl. No. 13/071,183.
Office action dated Nov. 6, 2013 for U.S. Appl. No. 13/071,198.
Office action dated Nov. 26, 2013 for U.S. Appl. No. 13/071,239.
Patent Examination Report No. 1 for corresponding Australian Patent Application No. 2011232357 dated Dec. 3, 2014, 2 pages.
Patent Examination Report No. 1 for corresponding Australian Patent Application No. 2011232358 dated Dec. 5, 2014, 2 pages.
Patent Examination Report No. 1 for corresponding Australian Patent Application No. 2011232360 dated Dec. 9, 2014, 2 pages.
Patent Examination Report No. 1 for corresponding Australian Patent Application No. 2011232361 dated Dec. 12, 2014, 3 pages.
Patent Examination Report No. 1 for corresponding Australian Patent Application No. 2011232362 dated Jan. 11, 2015, 2 pages.
Supplementary European Search Report for EP 09816963.4 dated Aug. 21, 2015, 5 pages.
Supplementary European Search Report for EP 11760253.2, dated Feb. 22, 2017, 8 pages.
Supplementary European Search Report for EP 11760254.0, dated Apr. 12, 2017, 7 pages.

(56) References Cited

OTHER PUBLICATIONS

Supplementary European Search Report for EP 11760256.5, dated Aug. 12, 2016, 9 pages.
Supplementary European Search Report for EP 11760258.1 dated Dec. 5, 2016, 9 pages.
Supplementary European Search Report for EP 12744749.8, dated Apr. 7, 2016, 11 pages.
Supplementary European Search Report for EP 12744813.2, dated Nov. 25, 2015, 10 pages.
Supplementary Extended European Search Report for EP 11760257 dated Sep. 23, 2015, 6 pages.
The International Search Report and Written Opinion of the International Searching Authority for Application No. PCT/US11/29859, dated May 6, 2011.
The International Search Report Written Opinion of the International Searching Authority for Application No. PCT/US11/29861, dated May 8, 2011.
"U.S. Appl. No. 14/621,231, Notice of Allowance dated Nov. 16, 2018", 8 pgs.
"U.S. Appl. No. 14/294,631, Notice of Allowance dated Nov. 16, 2018", 8 pgs.
"U.S. Appl. No. 16/251,691, Preliminary Amendment filed Jan. 21, 2019", 3 pgs.
"U.S. Appl. No. 16/251,767, Preliminary Amendment filed Jan. 21, 2019", 3 pgs.
"U.S. Appl. No. 16/251,691, Non Final Office Action dated Aug. 7, 2020", 15 pgs.
"U.S. Appl. No. 14/313,742, Examiner Interview Summary dated Jul. 14, 2017", 4 pgs.
"U.S. Appl. No. 14/313,742, Examiner Interview Summary dated Dec. 7, 2016", 3 pgs.
"U.S. Appl. No. 14/313,742, Response filed Apr. 29, 2016 to Non Final Office Action dated Jan. 29, 2016", 10 pgs.
"U.S. Appl. No. 14/313,742, Response filed Jul. 24, 2017 to Non Final Office Action dated Mar. 24, 2017", 12 pgs.
"U.S. Appl. No. 14/313,742, Response filed Dec. 12, 2016 to Final Office Action dated Aug. 12, 2016", 10 pgs.
"U.S. Appl. No. 15/831,110, Notice of Allowance dated Feb. 6, 2020", 9 pgs.
"U.S. Appl. No. 15/831,110, Response filed Jan. 20, 2020 to Non Final Office Action dated Oct. 18, 2019", 8 pgs.
"U.S. Appl. No. 16/251,691, Notice of Allowance dated Oct. 15, 2020", 9 pgs.
"U.S. Appl. No. 16/251,691, Response filed Sep. 30, 2020 to Non Final Office Action dated Aug. 7, 2020", 7 pgs.
"U.S. Appl. No. 16/251,691, Supplemental Notice of Allowability dated Jan. 6, 2021", 2.
"U.S. Appl. No. 16/251,691, Supplemental Notice of Allowability dated Nov. 24, 2020", 2 pgs.
"U.S. Appl. No. 16/251,767, Non Final Office Action dated Oct. 9, 2020", 9 pgs.
"U.S. Appl. No. 16/251,767, Non Final Office Action dated Oct. 20, 2020", 10 pgs.
"U.S. Appl. No. 16/251,767, Response filed Jan. 19, 2021 to Non Final Office Action dated Oct. 20, 2020", 6 pgs.

\* cited by examiner

PARTIALLY CRIMPED STENT

CROSS-REFERENCES TO RELATED APPLICATIONS

The present application is a Continuation of U.S. Ser. No. 14/317,387 filed Jun. 27, 2014 (Allowed); which is a Divisional of U.S. Ser. No. 13/071,149 filed Mar. 24, 2011 (now U.S. Pat. No. 8,821,562); which is a Continuation of PCT Appln. No. PCT/US2009/058505 filed Sep. 25, 2009; which claims the benefit of U.S. Provisional Appln. No. 61/194,346 filed Sep. 25, 2008; the entire contents which are incorporated herein by reference in their entirety for all purposes.

The present application is related to U.S. application Ser. No. 13/071,251 (now U.S. Pat. No. 8,979,917); Ser. No. 13/071,239 (now U.S. Pat. No. 8,769,796); Ser. No. 13/071,198 (now U.S. Pat. No. 8,795,347); Ser. No. 13/071,183 (now U.S. Pat. No. 8,808,347); and Ser. No. 13/071,162 (now U.S. Pat. No. 8,828,071), all of which were filed on Mar. 24, 2011 and are incorporated herein by reference in their entirety for all purposes. The present application is also related to U.S. Provisional Appln. Nos. 61/317,198; 61/317,114; 61/317,121; and 61/317,130; all of which were filed on Mar. 24, 2010, and are incorporated herein by reference in their entirety for all purposes.

BACKGROUND OF THE INVENTION

The present invention relates to the field of medical stents and, more particularly, for the treatment of lesions and other problems in or near a vessel bifurcation. A stent is an endoprosthesis scaffold or other device that typically is intraluminally placed or implanted within a vein, artery, or other tubular body organ for treating an occlusion, stenosis, aneurysm, collapse, dissection, or weakened, diseased, or abnormally dilated vessel or vessel wall, by expanding the vessel or by reinforcing the vessel wall. In particular, stents are quite commonly implanted into the coronary, cardiac, pulmonary, neurovascular, peripheral vascular, renal, gastrointestinal and reproductive systems, and have been successfully implanted in the urinary tract, the bile duct, the esophagus, the tracheo-bronchial tree and the brain, to reinforce these body organs. Two important current widespread applications for stents are for improving angioplasty results by preventing elastic recoil and remodeling of the vessel wall and for treating dissections in blood vessel walls caused by balloon angioplasty of coronary arteries, as well as peripheral arteries, by pressing together the intimal flaps in the lumen at the site of the dissection. Conventional stents have been used for treating more complex vascular problems, such as lesions at or near bifurcation points in the vascular system, where a secondary artery branches out of a typically larger, main artery, with limited success rates.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or pattern has strut and connecting balloon catheter portions that impede blood flow at bifurcations.

Furthermore, the configuration of struts and connecting balloon catheter portions may obstruct the use of post-operative devices to treat a daughter vessel in the region of a vessel bifurcation. For example, deployment of a first stent in the mother lumen may prevent a physician from inserting a daughter stent through the ostium of a daughter vessel of a vessel bifurcation in cases where treatment of the mother vessel is suboptimal because of displaced diseased tissue (for example, due to plaque shifting or "snow plowing"), occlusion, vessel spasm, dissection with or without intimal flaps, thrombosis, embolism, and/or other vascular diseases.

A regular stent is designed in view of conflicting considerations of coverage versus access. For example, to promote coverage, the cell structure size of the stent may be minimized for optimally supporting a vessel wall, thereby preventing or reducing tissue prolapse. To promote access, the cell size may be maximized for providing accessibility of blood flow and of a potentially future implanted daughter stent to daughter vessels, thereby preventing "stent jailing," and minimizing the amount of implanted material. Regular stent design has typically compromised one consideration for the other in an attempt to address both. Problems the present inventors observed involving daughter jailing, fear of plaque shifting, total occlusion, and difficulty of the procedure are continuing to drive the present inventors' into the development of novel, delivery systems, which are easier, safer, and more reliable to use for treating the above-indicated variety of vascular disorders.

Although conventional stents are routinely used in clinical procedures, clinical data shows that these stents are not capable of completely preventing in-stent restenosis (ISR) or restenosis caused by intimal hyperplasia. In-stent restenosis is the reoccurrence of the narrowing or blockage of an artery in the area covered by the stent following stent implantation. Patients treated with coronary stents can suffer from in-stent restenosis.

Many pharmacological attempts have been made to reduce the amount of restenosis caused by intimal hyperplasia. Many of these attempts have dealt with the systemic delivery of drugs via oral or intravascular introduction. However, success with the systemic approach has been limited.

Systemic delivery of drugs is inherently limited since it is difficult to achieve constant drug delivery to the afflicted region and since systemically administered drugs often cycle through concentration peaks and valleys, resulting in time periods of toxicity and ineffectiveness. Therefore, to be effective, anti-restenosis drugs should be delivered in a localized manner.

One approach for localized drug delivery utilizes stents as delivery vehicles. For example, stents seeded with transfected endothelial cells expressing bacterial beta-galactosidase or human tissue-type plasminogen activator were utilized as therapeutic protein delivery vehicles. See, e.g., Dichek, D. A. et al., "Seeding of Intravascular Stents With Genetically Engineered Endothelial Cells," Circulation, 80:1347-1353 (1989).

U.S. Pat. No. 5,679,400, International Patent Application WO 91/12779, entitled "Intraluminal Drug Eluting Prosthesis," and International Patent Application WO 90/13332, entitled "Stent With Sustained Drug Delivery" disclose stent devices capable of delivering antiplatelet agents, anticoagulant agents, antimigratory agents, antimetabolic agents, and other anti-restenosis drugs.

U.S. Pat. Nos. 6,273,913, 6,383,215, 6,258,121, 6,231,600, 5,837,008, 5,824,048, 5,679,400 and 5,609,629 teach stents coated with various pharmaceutical agents such as Rapamycin, 17-beta-estradiol, Taxol and Dexamethasone. This and all other referenced patents are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

BRIEF SUMMARY OF THE INVENTION

The present invention relates to delivery catheters for delivery of stents for placement at vessel bifurcations and is generally configured to at least partially cover a portion of a daughter vessel as well as a mother vessel. The invention comprises stent crimping methods to differentially crimp a stent to account for stent design elements such as a tapered stent that does not have uniform walls. Additionally, differential crimping can be applied to stents that are mounted on two catheters.

BRIEF DESCRIPTION OF THE DRAWINGS

The invention is herein described, by way of example only, with reference to the accompanying drawings. With specific reference now to the drawings, it is stressed that the particulars shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the invention may be embodied in practice. In the drawings.

DETAILED DESCRIPTION OF THE INVENTION

Figure 1:
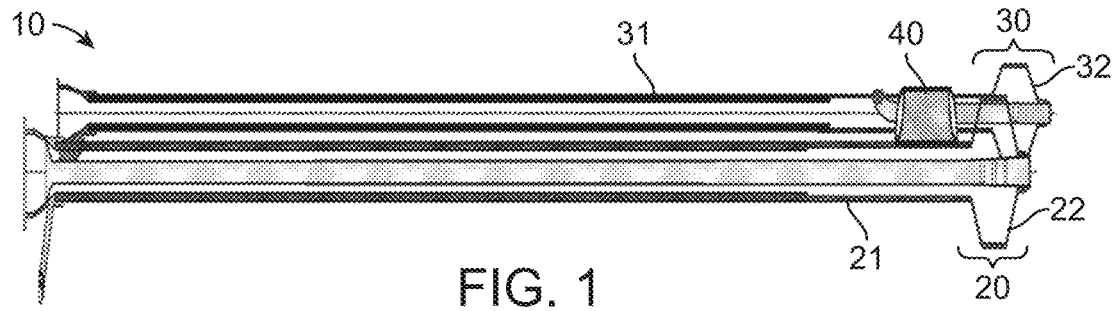
FIG. 1 is a cross sectional view of one embodiment with the mother catheter an over the wire design and the daughter catheter with a rapid exchange.

The present invention relates to delivery catheters for delivery of stents for placement at vessel bifurcations and is generally configured to at least partially cover a portion of a daughter vessel as well as a mother vessel. In particular, the present invention relates to novel methods of crimping stents to delivery catheters.

A variety of catheter designs may be employed to deploy and position the mother and daughter stents. Such catheters may be used in connection with multiple guidewires that terminate in the mother and daughter vessels. These guidewires may be used to facilitate introduction of the catheter, any angioplasty balloons, any stents, and/or to properly orient the stent or balloon within the vessel.

In general, the methods of the invention may utilize a catheter system comprising a catheter body having a mother vessel guidewire lumen and a daughter vessel balloon that is independently operable and coupled to the catheter body. The daughter balloon catheter portion has a daughter vessel guidewire lumen. The catheter system further includes mother catheter balloon, and a stent is disposed over the balloon. The daughter catheter portion extends into the proximal opening of the mother stent and exits the mother stent through a side passage of the mother stent.

According to one method, a mother vessel guidewire is inserted into the mother vessel until a distal end of the mother vessel guidewire passes beyond the ostium of the daughter vessel, and a daughter vessel guidewire is inserted into the mother vessel until a distal end of the daughter vessel guidewire passes into the daughter vessel. To prevent the crossing of guidewires, the two vessels are wired through a guidewire catheter with two lumens to keep the guidewires separate and untangled. This guidewire catheter is then removed and a wire separator is placed on the wires to keep the guidewires unwrapped. The catheter system is then advanced over the mother and daughter vessel guidewires, with the mother and daughter vessel catheters passing over the mother vessel guidewire and the daughter vessel guidewire. The catheter system is advanced on both wires with the daughter vessel balloon catheter portion distal to the mother balloon catheter portion. As the catheter system advances over the wires, the daughter vessel balloon will enter the daughter vessel and may be deployed immediately or simultaneously with the mother vessel balloon after placement of the mother vessel balloon. The mother balloon catheter portion of the catheter system is then advanced distally as far as it can be advanced to the bifurcation site because the tension of the daughter catheter on the mother stent will prevent the mother catheter from moving distally. This method facilitates advancement of the catheter system to the bifurcation, which may be necessary for tortuous or calcified coronaries. Once the catheter system is in place the daughter vessel balloon catheter portion is then pulled back relative to the mother catheter so that it is partially within the mother stent, alignment can be performed with radiopaque markers. The operator can then gently push the catheter system distal to maximize apposition to the carina. The daughter balloon is then inflated to ensure proper alignment of the mother stent. The daughter balloon may also have a stent on its distal portion, which would result in the proximal portion of the mother stent and the daughter stent to expand simultaneously. The daughter balloon is then deflated. The mother balloon is then inflated which deploys the mother stent. Kissing, reinflation, of the two balloons is done if necessary or for shifting plaque. The catheter system may be removed while the wires remain in place. The daughter vessel can be stented if necessary with any commercially available stent for example a short stent that would not cover the entire daughter balloon. The two vessels may be angioplastied separately as necessary predilatation is indicated on occasion.

In an alternative method, the mother catheter can be mounted on the daughter vessel guidewire and the daughter catheter can be mounted on the mother vessel guidewire. In daughter vessels with a high degree of angularity, over 60-70%, the friction is lower when the operator needs to draw the daughter stent proximal and into the mother stent in this configuration. The catheter system is advanced so the daughter balloon catheter can pass the ostium of the daughter vessel and remain in the mother vessel. As the catheter system is advanced further, the mother balloon catheter will enter the daughter vessel. The catheter system can only be advanced to the bifurcation because there is tension between the daughter catheter in the mother vessel and mother stent on the mother catheter that prevents further advancement. While the mother catheter is held in place, the daughter catheter is drawn back such that the proximal portion of the daughter balloon is in the mother stent. Alignment is performed with radiopaque markers. The operator can then gently push the catheter system distal to maximize apposition to the carina. A stent on the daughter balloon is aligned so that when the daughter balloon is inflated the daughter stent and the proximal portion of the mother stent expand simultaneously and give complete coverage of the mother vessel. The daughter vessel balloon is then deflated. The mother vessel balloon is then inflated and the distal portion of the mother stent is expanded. A kissing procedure can also be performed if required.

In an alternative embodiment, the system can be used for provisional stenting of the daughter vessel. The catheter system comprising mother catheter comprising a mother balloon and mother stent, and a daughter catheter comprising a daughter balloon wherein the mother catheter is loaded onto a daughter vessel guidewire and the daughter catheter is loaded onto the mother vessel guidewire. The catheter system is advanced so the daughter balloon catheter can pass the ostium of the daughter vessel and remain in the mother vessel. As the catheter system is advanced further, the mother catheter and mother stent will enter the daughter vessel. The catheter system can only be advanced to the bifurcation because there is tension between the daughter catheter in the mother vessel and mother stent on the mother catheter that prevents further advancement. While the mother catheter is held in place, the daughter catheter is drawn back such that the proximal portion of the daughter balloon is in the mother stent. Alignment is performed with radiopaque markers. The operator can then gently push the catheter system distal to maximize apposition to the carina. A balloon on a wire could be used as an alternative to the daughter catheter.

In an alternative embodiment, the system can be used for provisional stenting of the daughter vessel. The catheter system comprising; a mother catheter comprising a mother balloon and, a daughter catheter comprising a daughter balloon and a daughter stent on the distal portion of the daughter balloon wherein the mother catheter is loaded onto a mother vessel guidewire and the daughter catheter is loaded onto the daughter vessel guidewire. The catheter system is advanced on both wires with the daughter balloon catheter portion distal to the mother balloon catheter portion. As the catheter system advances over the wires, the daughter balloon will enter the daughter vessel. The mother balloon catheter portion of the catheter system is then advanced distally as far as it can be advanced to the bifurcation. Once the catheter system is in place the daughter vessel balloon catheter portion is then pulled back relative to the mother catheter so that it is partially within the mother vessel, alignment can be performed with radiopaque markers. The operator can then gently push the catheter system distal to maximize apposition to the carina. The daughter balloon and mother balloon are simultaneously inflated. The mother vessel can be stented if necessary with any commercially available stent. A balloon on a wire could be used as an alternative to the daughter catheter.

In an alternative embodiment, the catheter system can be arranged with the daughter balloon portion proximal to the mother balloon portion forward over the guidewires to the bifurcation. In the case of the mother catheter on the mother guidewire, the alignment of the mother stent with the ostium of the daughter vessel occurs because tension between the daughter guidewire and mother stent on the mother catheter that prevents further advancement of the mother catheter. In the alternative case of the mother catheter on the daughter guidewire, the alignment of the mother stent with the ostium of the mother vessel occurs because tension between the mother guidewire and mother stent on the mother catheter that prevents further advancement of the mother catheter. In both cases the daughter stent is advanced distally into alignment with the mother stent and expanded.

Figure 4:
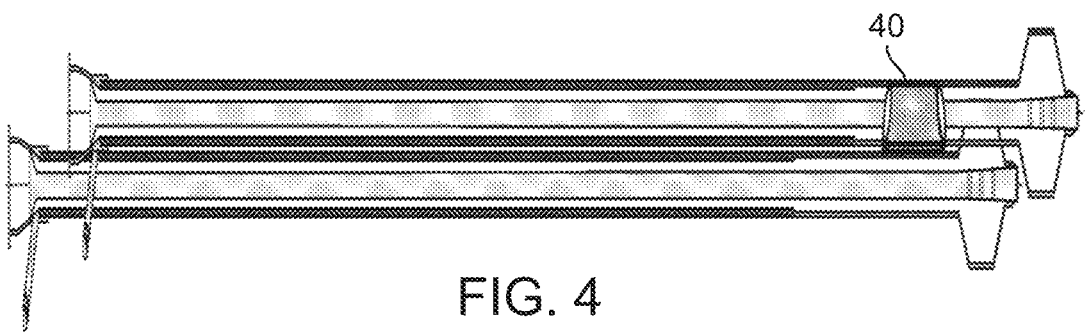
FIG. 4 is a cross sectional view of one embodiment with both mother and daughter catheters with an over the wire design.

In preferred embodiments, FIGS. 1 and 4 show the mother catheter is an Over-the-Wire (OTW) design and the daughter catheter is a Rapid-Exchange (RX) design with daughter catheter portion about 3 centimeters distal the mother catheter portion. The daughter balloon is placed just distal to the tip of the mother catheter, this arrangement minimizes the overall profile of the catheter system and allows maximal tracking of the arteries. The system may additionally have stents crimped over the balloons. The daughter stent may be approximately half the length of the daughter balloon or mother stent. The proximal end of the mother stent may be crimped only slightly to allow the daughter catheter balloon portion to operate independently, i.e. may be pushed or pulled without dislodging the mother stent. The method comprising the following steps:

1. Advance the catheter system to bifurcation, daughter balloon catheter portion and mother balloon catheter portion in their respective vessels. The mother catheter is no longer able to advance because of the tension between the mother stent and daughter catheter.

2. The daughter balloon proximal portion is drawn back into the mother stent and aligned with radiopaque markers.

3. While holding both the mother and daughter catheters tightly, the operator pushes forward lightly.

4. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.

5. Once the daughter stent is fully deployed, then the mother balloon can be fully expanded to deploy the distal portion of the mother stent.

6. A conventional Kissing procedure may be utilized to ensure full apposition.

In one particular aspect, the daughter balloon catheter portion may be used without a stent. This would allow perfect alignment of mother stent around the ostium of the daughter vessel. The daughter balloon would be used for the alignment as outlined in step three above, and expand the proximal portion of the mother stent.

Figure 5:
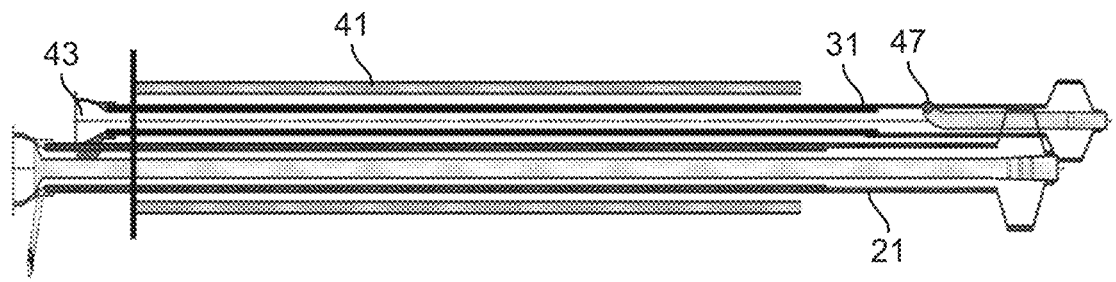
FIG. 5 is a cross sectional view of one embodiment with the mother catheter an over the wire design, the daughter catheter with a rapid exchange, and a capture tube.

In an alternative embodiment, FIG. 5 shows the mother catheter is an Over-the-Wire (OTW) design and the daughter catheter is a Rapid-Exchange (RX) design with daughter catheter balloon portion about 3 centimeters distal the mother catheter balloon portion. The system may additionally have stents crimped over the balloons. The daughter stent may be approximately half the length of the mother balloon or stent. The proximal end of the mother stent may be crimped only slightly to allow the daughter catheter balloon portion to operate independently, so that it may be pushed or pulled without dislodging the mother stent. The method comprising the following steps:

1. Looping the OTW so that one operator can hold both guide wires with one hand and then push both catheters with the other.

2. Advance the catheter system to bifurcation, daughter balloon catheter portion and mother balloon catheter portion aligned in their respective vessels, as disclosed in steps two through three in the above embodiment.

3. While holding both the mother and daughter catheters tightly, push the catheter system forward until the mother balloon catheter portion is stopped at the carina.

4. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.

5. Once the daughter stent is fully deployed, then the mother balloon can be fully expanded to deploy the distal portion of the mother stent.

6. A conventional Kissing procedure may be utilized to ensure full apposition.

In one particular aspect, the daughter balloon catheter portion may be used without a stent. This would allow perfect alignment of mother stent around the ostium of the daughter vessel. The daughter balloon would be used for the alignment as outlined in step three above, and expand the proximal portion of the mother stent.

In an alternative embodiment, the mother catheter is an Over-the-Wire design and the daughter catheter is a Rapid-Exchange design with daughter catheter portion about 3 centimeters distal. The system may additionally have stents crimped over the balloons. The daughter stent may be approximately half the length of the mother balloon or stent. The proximal end of the mother stent may be crimped only slightly to allow the daughter catheter balloon portion to operate independently, i.e. may be pushed or pulled without dislodging the mother stent. The method comprising the following steps:

1. Place the daughter guidewire only and then slide the system into the guide catheter. Just before exiting the guide catheter, insert the mother guide wire through the catheter and into the mother vessel, then push the system out of the guide catheter. To reduce wire wrap.

2. Advance the catheter system to the bifurcation, daughter balloon catheter portion and mother balloon catheter portion aligned in their respective vessels.

3. Advance the catheter system to bifurcation, daughter balloon catheter portion and mother balloon catheter portion aligned in their respective vessels, as disclosed in step two in the above embodiment.

4. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.

5. Once the daughter stent is fully deployed, then the mother balloon can be fully expanded to deploy the distal portion of the mother stent.

6. A conventional Kissing procedure may be utilized to ensure full apposition.

In one particular aspect, the daughter balloon catheter portion may be used without a stent. This would allow perfect alignment of mother stent around the ostium of the daughter vessel. The daughter balloon would be used for the alignment as outlined in step three above, and expand the proximal portion of the mother stent.

In an alternative embodiment the mother and daughter systems balloons are aligned. This embodiment could include the mother stent and daughter stent or either stent. When there is both a mother stent and a daughter stent, the daughter stent would be approximately half the length of the mother stent so that the daughter stent could be mounted on the distal half of the daughter balloon. Further the proximal portion of the daughter catheter would be crimped under the mother stent. The dual stent arrangement would reduce the profile compared to a full length stent that covered the entire length of the daughter balloon.

The methods described herein could alternatively include the step of flushing the catheters and the guidewire port to assist with maneuverability. The methods described herein could alternatively include the step of a couple of snap-on couplers the catheters are locked together.

In another particular aspect, each balloon catheter portion may include at least one radiopaque marker. With such a configuration, separation of the markers may be conveniently observed using fluoroscopy to indicate that the balloon catheter portions have passed beyond the ostium and the daughter balloon catheter portion has passed into the daughter vessel, thus aligning the passage of the stent with the ostium of the daughter vessel.

In another particular aspect, the catheter systems design is contemplated to cover combinations of rapid exchange and over the wire; for visualization purposes the hybrid versions are preferred because they are easier to distinguish while using fluoroscopy.

In another particular aspect, the proximal balloon may be differentially expandable, such that one end of the balloon may expand prior to the other end. In another particular aspect, the proximal balloon catheter portion may receive a stent that can be crimped under variable pressure to allow the distal balloon catheter portion freedom of movement.

In another particular aspect, a stent may be crimped over the proximal balloon catheter portion and the stent may be designed to deploy with variable profile to better oppose the patient anatomy.

In another particular aspect, the distal balloon catheter portion may be delivered via a pull away.

All of the above embodiments may utilize mother vessel stents ranging from 2.5 to 5.0 millimeter in diameter and daughter vessel stent ranging from 2.0 to 5.0 millimeter in diameter. The length of the stents could be in the range of 4 to 40 millimeter. The position of a stent on a catheter is not fixed and can be positioned on either or both catheters.

FIG. 1 illustrates the catheter system 10 with a distal daughter balloon catheter portion 30 comprising a balloon 32 with a daughter stent 33 crimped (not shown). The daughter stent 33 may be shorter than the mother stent 23. In a particular embodiment the daughter stent 33 is half the length of the mother stent 23 (not shown). The distal daughter stent 33 is crimped under standard conditions known in the art. The proximal mother balloon catheter portion 20 comprises a mother balloon 22 and a mother stent 23. The mother stent 23 is crimped differentially along the longitudinal direction and circumferentially, FIGS. 36-37. In the particular embodiment, the distal half 23a of the mother stent 23 is crimped under typical conditions to ensure that the mother stent 23 is not dislodged during the alignment with the distal daughter balloon 32. Further, the proximal portion 23b of the mother stent 23 is crimped under non-standard, relatively loose, conditions to allow the distal daughter balloon catheter portion 30 freedom of movement even though a portion of the daughter balloon catheter portion 30 is circumferentially enclosed. The mother catheter 21 and daughter catheter 31 are slidably attached to each other via a hollow exchange port 40. The exchange port 40 is embedded in the side of the mother over the wire catheter. The exchange port 40 is 10 centimeters long with a diameter just large enough to allow the insertion of the rapid exchange daughter catheter and daughter 31 balloon 32. The exchange port 40 can vary in length from 1 centimeter to 30 centimeters. The entry for the daughter catheter 32 on the exchange port 40 is proximal and the exit for the daughter catheter 32 is on the distal end of the exchange port 40. The daughter catheter 32 is loaded through the exchange port 40 and the daughter balloon 32 extends distally 5 centimeters from the exit of the exchange port 40 5 centimeters. However, it is possible to have the exchange port 40 1 to 30 centimeters proximal to the mother balloon 22. The mother stent 23 can be crimped on to the balloon after it has been loaded through the exchange port 40. The exchange port 40 must have a tight fit to reduce catheter profile and have low friction to allow the operator to easily slide the catheters relative to each other.

Figure 2:
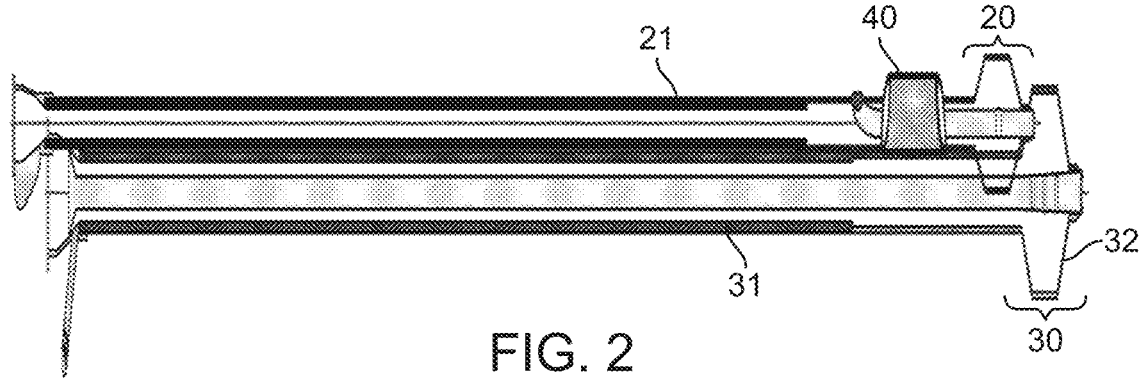
FIG. 2 is a cross sectional view of one embodiment with the daughter catheter an over the wire design and the mother catheter with a rapid exchange.

FIG. 2 illustrates a cross sectional view of one embodiment with the mother catheter balloon portion 20 proximal to the daughter catheter balloon portion 30 utilizing the same exchange port 40 as described in FIG. 1. The daughter balloon 32 is 5 centimeters distal from the exit of the exchange port 40. As disclosed above, the daughter balloon 32 could be distal from the exchange 40 port 1 to 30 centimeters.

Figure 3:
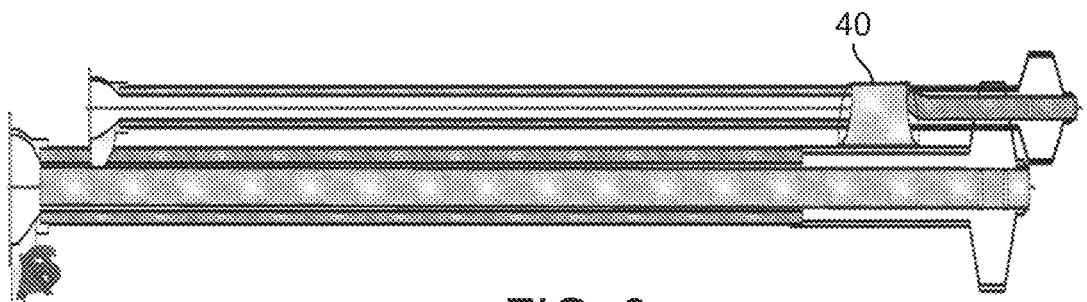
FIG. 3 is a cross sectional view of one embodiment with both mother and daughter catheters with rapid exchange design.

FIG. 3 illustrates a cross sectional view of one embodiment with the mother and daughter catheters both having a rapid exchange design. In this particular embodiment one of the catheters has an exchange port 40 embedded in its side and the other catheter is loaded through the exchange port 40. Typically, the catheter would have to be loaded prior to having a stent crimped over the balloon portion.

FIG. 4 illustrates a cross sectional view of one embodiment with the mother and daughter catheters both having an over the wire design. In this particular embodiment one of the catheters has an exchange port 40 embedded in its side and the other catheter does not have an exchange port. The catheter without the exchange port would be loaded onto the catheter with an exchange port 40. Typically, the catheter would have to be loaded prior to having a stent crimped over the balloon portion.

Figure 6:
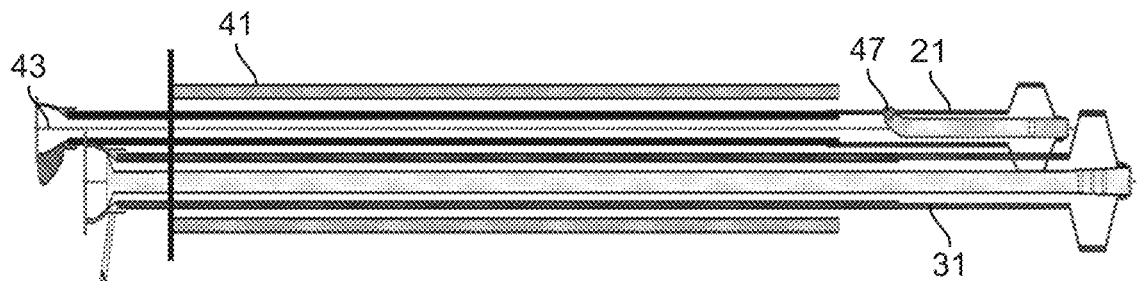
FIG. 6 is a cross sectional view of one embodiment with the daughter catheter an over the wire design, the mother catheter with a rapid exchange, and a capture tube.
Figure 7:
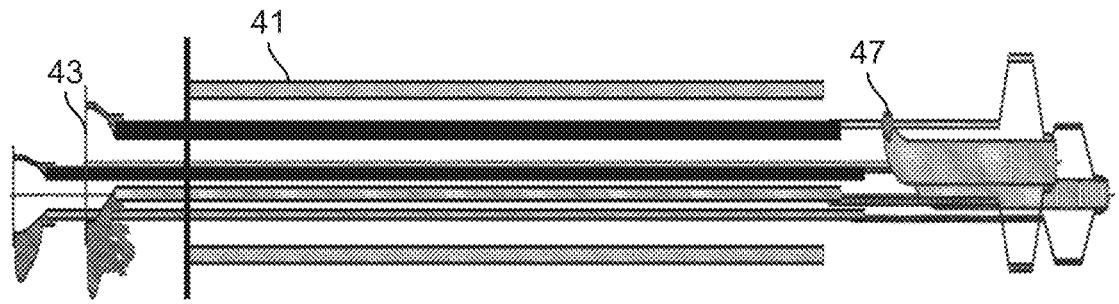
FIG. 7 is a cross sectional view of one embodiment with both mother and daughter catheters with rapid exchange design, and a capture tube.
Figure 8:
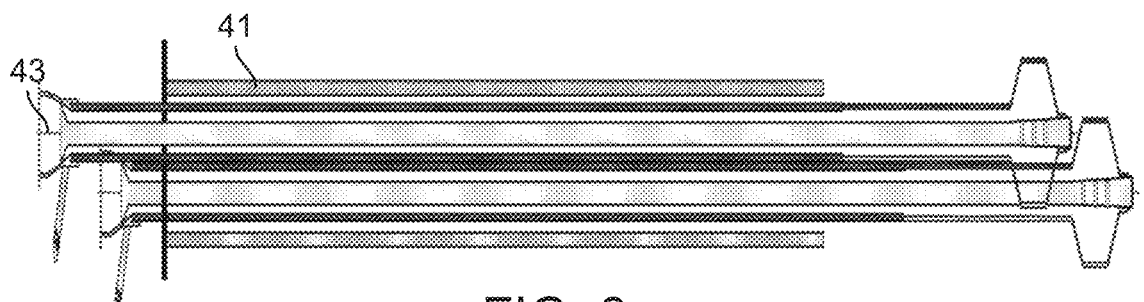
FIG. 8 is a cross sectional view of one embodiment with both mother and daughter catheters with an over the wire design, and a capture tube.

FIGS. 5-8 illustrate an end to end capture tube 41 that connects the catheters together. FIGS. 5-6 The capture tube 41 is a thin polymer hollow straw that covers the mother and daughter catheters from a point 10 centimeters distal the Indeflator® attachment 43 to a distal point that is 10 centimeters proximal from the rapid exchange catheter's proximal rapid exchange port 47. FIG. 7 discloses dual rapid exchange mother and daughter catheters so the end point of the capture tube 41 would be 10 centimeters proximal from the rapid exchange catheters' rapid exchange port 47 on the proximal catheter. FIG. 8 embodies a catheter system with dual over the wire designs, therefore the capture tube 41 ending point ends 30 centimeters proximal from the balloon portion of the most distal catheter. The capture tube 41 keeps the catheters from tangling. The capture tube 41 remains in place during the entire clinical procedure. FIG. 6 illustrates a distal daughter catheter 31 with an over the wire design and a proximal mother catheter 21 with a rapid exchange design. FIG. 5 illustrates a proximal mother catheter 21 with an over the wire design and a distal daughter catheter 31 with a rapid exchange design.

Figure 9:
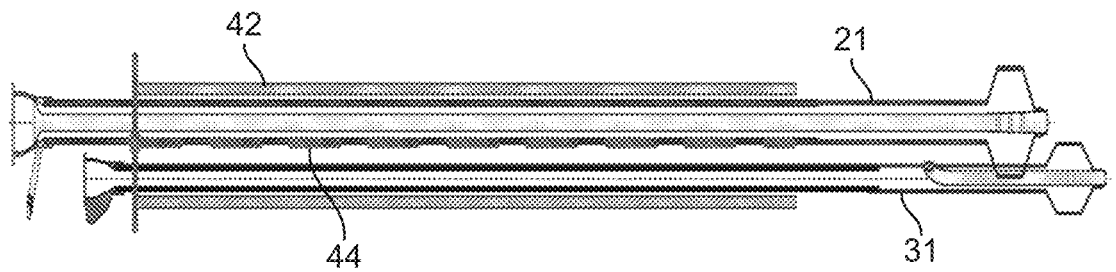
FIG. 9 is a cross sectional view of one embodiment with the mother catheter an over the wire design, the daughter catheter with a rapid exchange, and a removable capture tube.
Figure 10:
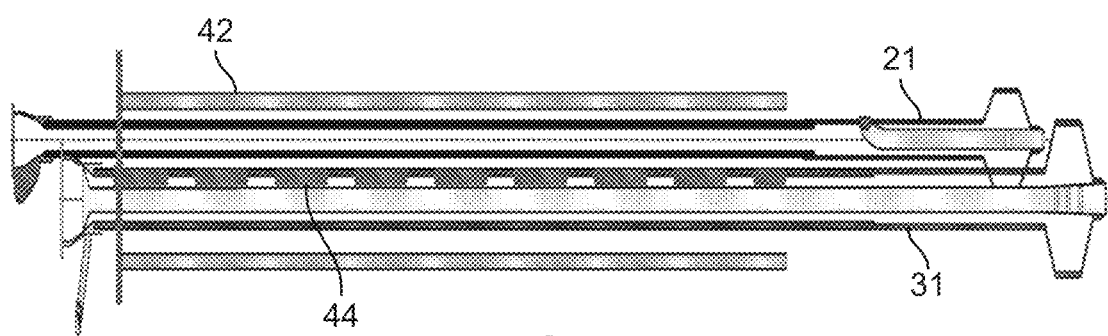
FIG. 10 is a cross sectional view of one embodiment with the daughter catheter an over the wire design, the mother catheter with a rapid exchange, and a removable capture tube.
Figure 11:
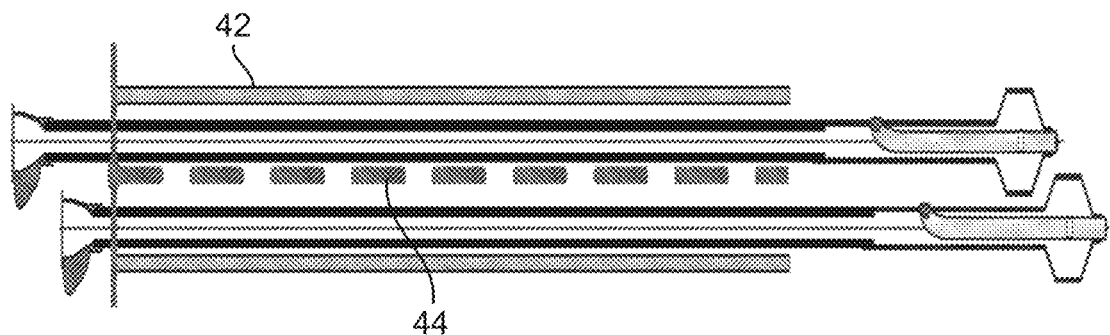
FIG. 11 is a cross sectional view of one embodiment with both mother and daughter catheters with rapid exchange design, and a capture tube.
Figure 12:
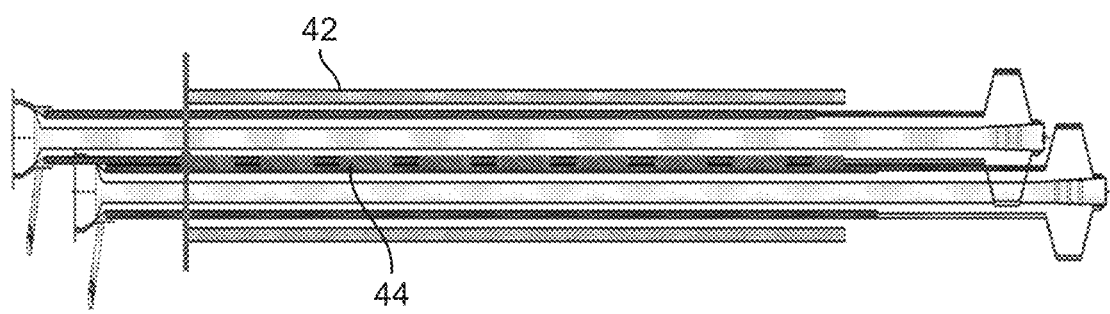
FIG. 12 is a cross sectional view of one embodiment with both mother and daughter catheters with an over the wire design, and a capture tube.

FIGS. 9-12 illustrate a removable capture tube 42 that is fitted over the dual catheters as described above but the capture tube 42 has a polymer appendage 44. Once the operator has the catheter system placed near the bifurcation the operator can grab hold of the polymer appendage 44 and pull the capture tube 42 off of the catheters. FIG. 10 illustrates a distal daughter catheter 31 with an over the wire design and a proximal mother catheter 21 with a rapid exchange design. FIG. 9 illustrates a proximal mother catheter 21 with an over the wire design and a distal daughter catheter 31 with a rapid exchange design. FIG. 11 illustrates a dual rapid exchange design with a removable capture tube 42. FIG. 12 illustrates a dual over the wire design with a removable capture tube 42.

Figure 13:
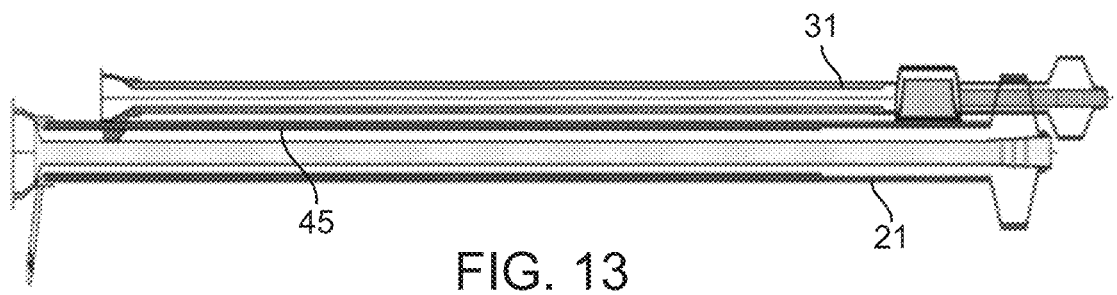
FIG. 13 is a cross sectional view of one embodiment with the mother catheter an over the wire design, the daughter catheter with a rapid exchange, and a short zipper.
Figure 14:
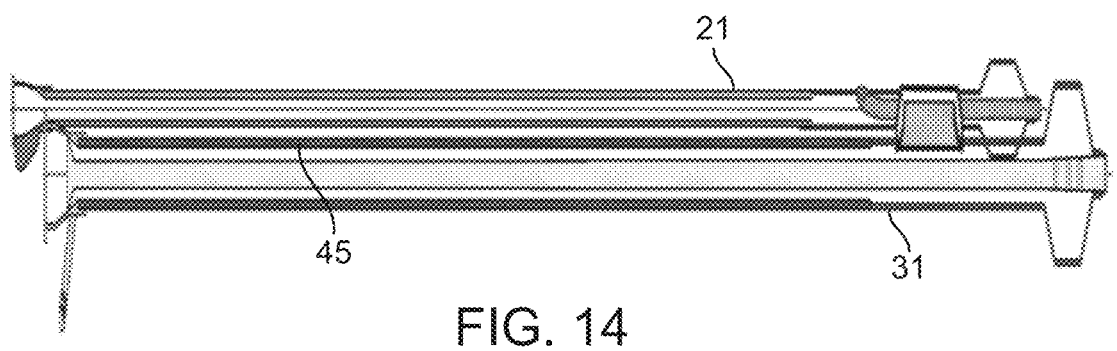
FIG. 14 is a cross sectional view of one embodiment with the daughter catheter an over the wire design, the mother catheter with a rapid exchange, and a short zipper.
Figure 15:
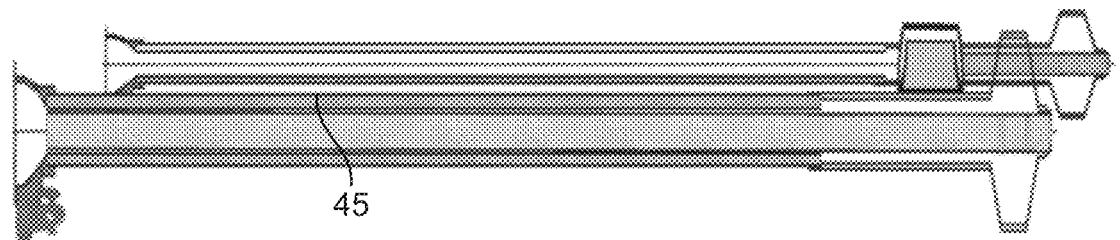
FIG. 15 is a cross sectional view of one embodiment with both mother and daughter catheters with rapid exchange design, and a short zipper.
Figure 16:
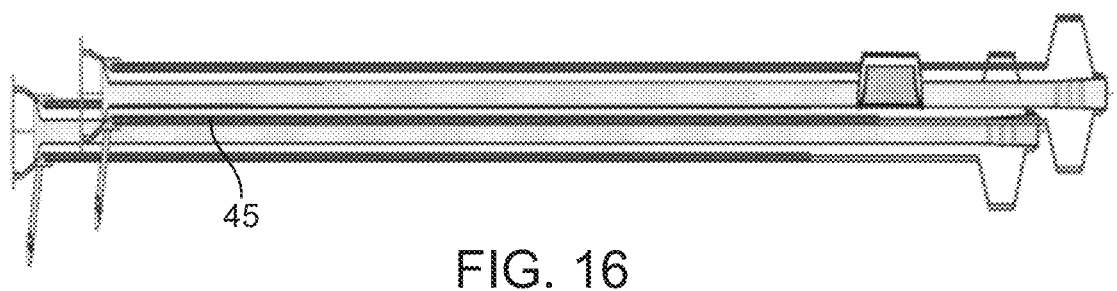
FIG. 16 is a cross sectional view of one embodiment with both mother and daughter catheters with an over the wire design, and a short zipper.
Figure 17:
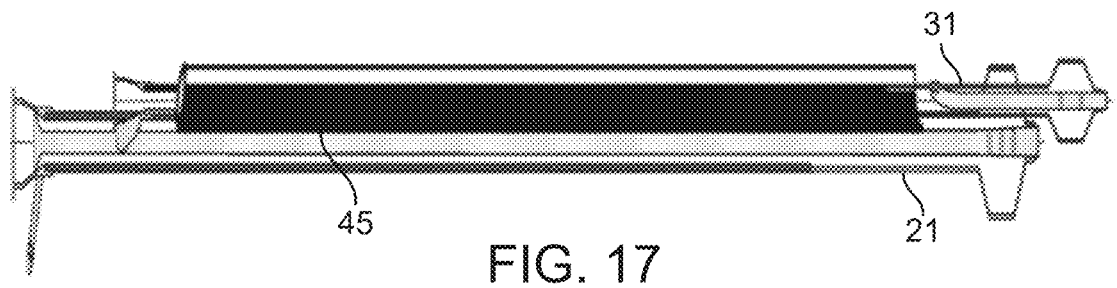
FIG. 17 is a cross sectional view of one embodiment with the mother catheter an over the wire design and the daughter catheter with a rapid exchange, and an end to end zipper.
Figure 18:
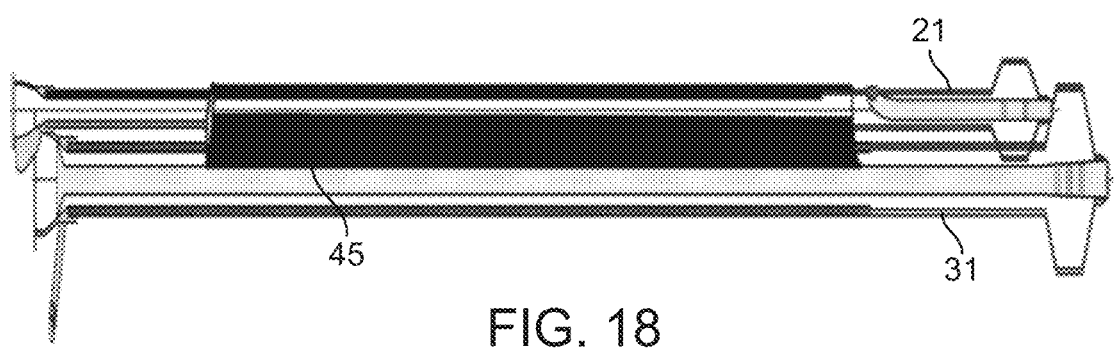
FIG. 18 is a cross sectional view of one embodiment with the daughter catheter an over the wire design, the mother catheter with a rapid exchange, and an end to end zipper.
Figure 19:
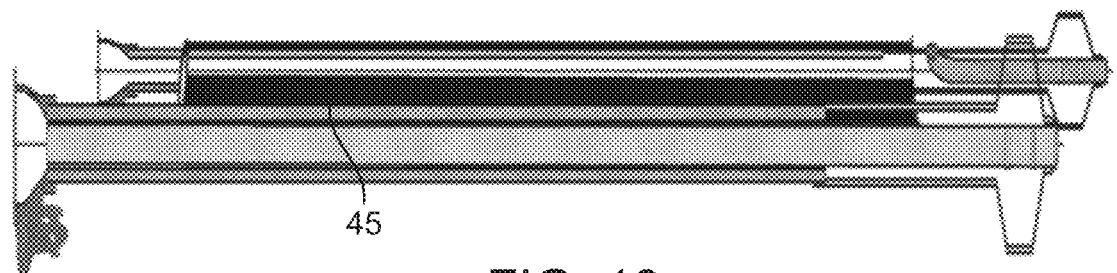
FIG. 19 is a cross sectional view of one embodiment with both mother and daughter catheters with rapid exchange design, and an end to end zipper.
Figure 20:
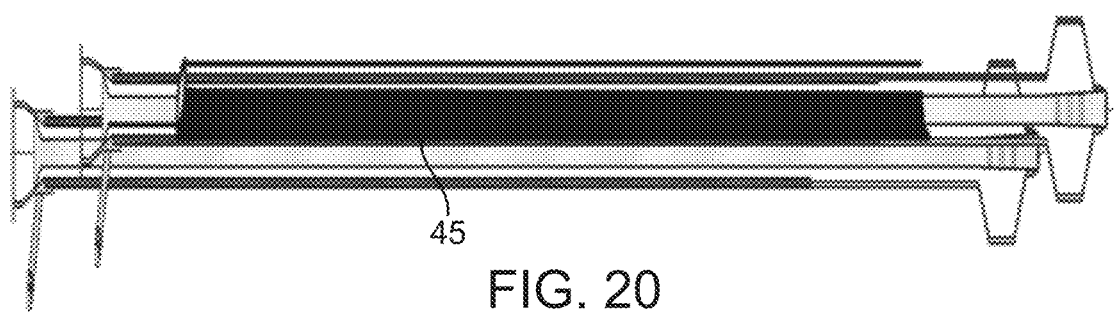
FIG. 20 is a cross sectional view of one embodiment with both mother and daughter catheters with an over the wire design, and an end to end zipper.

FIGS. 13-16 illustrate a zipper 45 that allows one catheter to snap in to the other catheter. The zipper 45 is essentially a groove that forms a concave receiving cross section and is carved into a catheter's outer surface in a straight line. The groove can be a single groove over a certain portion of a catheter or it can run from end to end. Alternatively, the catheter can have a series of short grooves of 1 to 10 centimeters in length that run the length of the catheter or only a certain portion. Full length end to end zippers will have reduced profile and reduced friction with the vessel. The resulting groove can receive another catheter and prevent the catheters from dislodging while the operator is advancing the catheters to the bifurcation. Once at the site the operator can still slidably move the catheters forward and back relative to each other. Mother catheters that utilize the groove can have fully crimped stents as described in several of the embodiments above; however, it is possible to allow operators to choose any commercially available catheter with or without a stent and mount the commercially available catheter via the zipper 45. The mother catheters with an empty zipper 45 would have a mother stent 23 full crimped on the distal balloon portion 22a of the mother catheter 21. After loading the commercially available catheter the operator would have to crimp the proximal portion of the mother stent 23b in situ prior to beginning the clinical procedure. This option may be extremely valuable to operators who can reduce their total inventory of catheters but have more options for treating bifurcated lesions. FIG. 14 illustrates a distal daughter catheter 31 with an over the wire design and a proximal mother catheter 21 with a rapid exchange design and a short zipper 45. FIG. 13 illustrates a proximal mother catheter 21 with an over the wire design and a distal daughter catheter 31 with a short zipper 45. FIG. 15 illustrates a dual rapid exchange design with a short zipper 45. FIG. 16 illustrates a dual over the wire design with a short zipper 45. FIG. 18 illustrates a distal daughter catheter 31 with an over the wire design and a proximal mother catheter 21 with a rapid exchange design and an end to end zipper 45. FIG. 17 illustrates a proximal mother catheter 21 with an over the wire design and a distal daughter catheter 31 with an end to end zipper 45. FIG. 19 illustrates a dual rapid exchange design with an end to end zipper 45. FIG. 20 illustrates a dual over the wire design with an end to end zipper 45.

Figure 21:
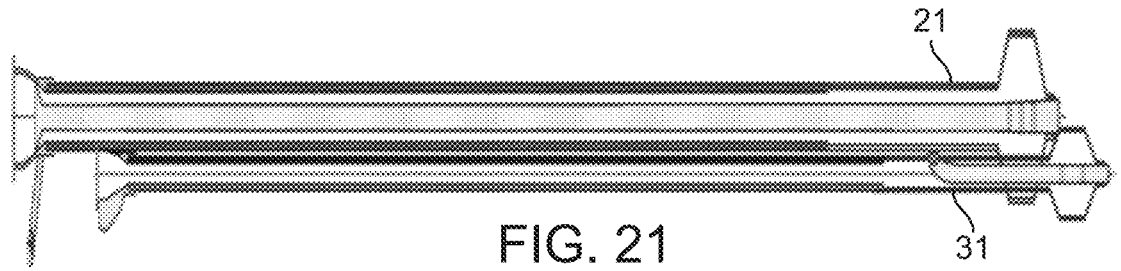
FIG. 21 is a cross sectional view of one embodiment with the mother catheter an over the wire design and the daughter catheter with a rapid exchange with a commercially available catheter.
Figure 22:
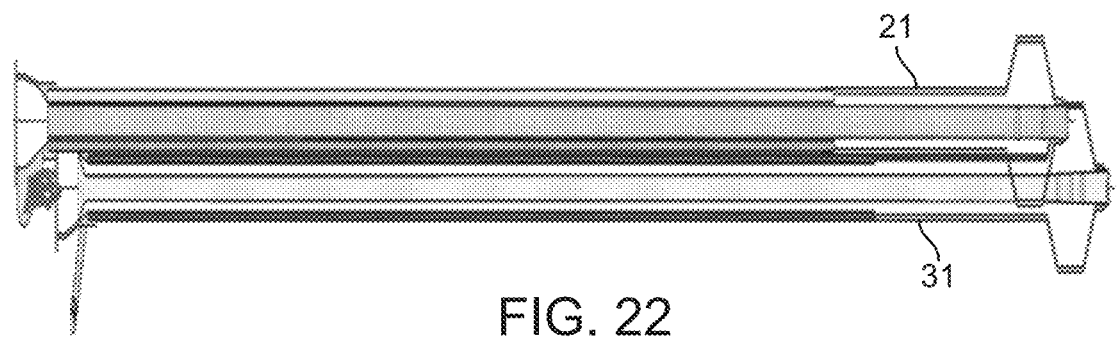
FIG. 22 is a cross sectional view of one embodiment with the daughter catheter an over the wire design and the mother catheter with a rapid exchange with a commercially available catheter.
Figure 23:
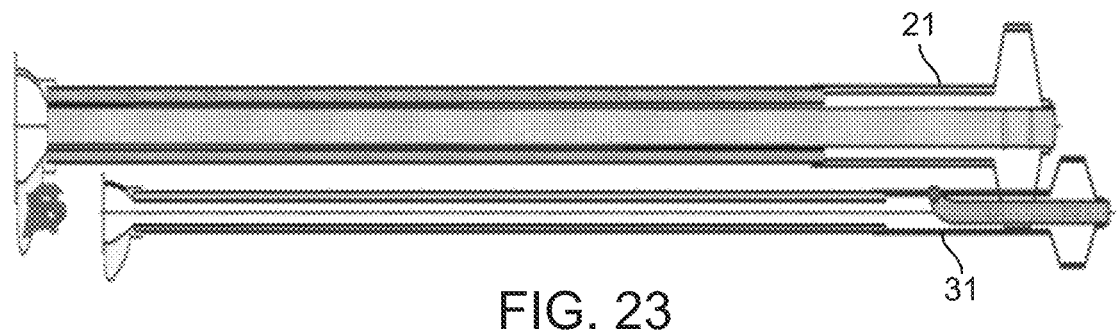
FIG. 23 is a cross sectional view of one embodiment with both mother and daughter catheters with rapid exchange design with a commercially available catheter.
Figure 24:
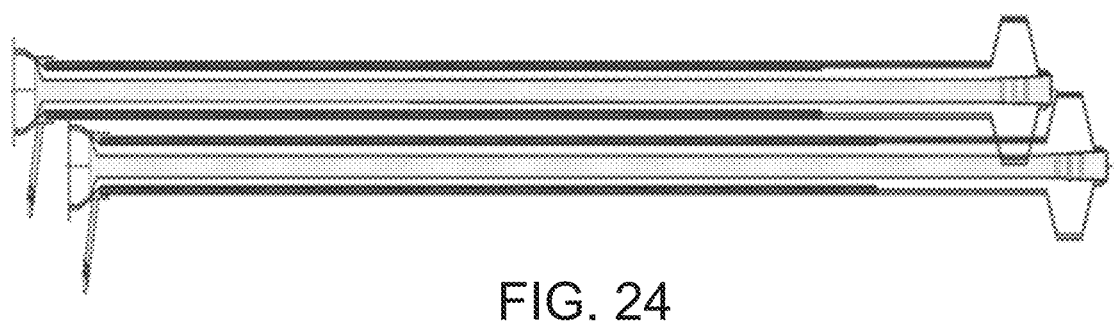
FIG. 24 is a cross sectional view of one embodiment with both mother and daughter catheters with an over the wire design with a commercially available catheter.
Figure 25:
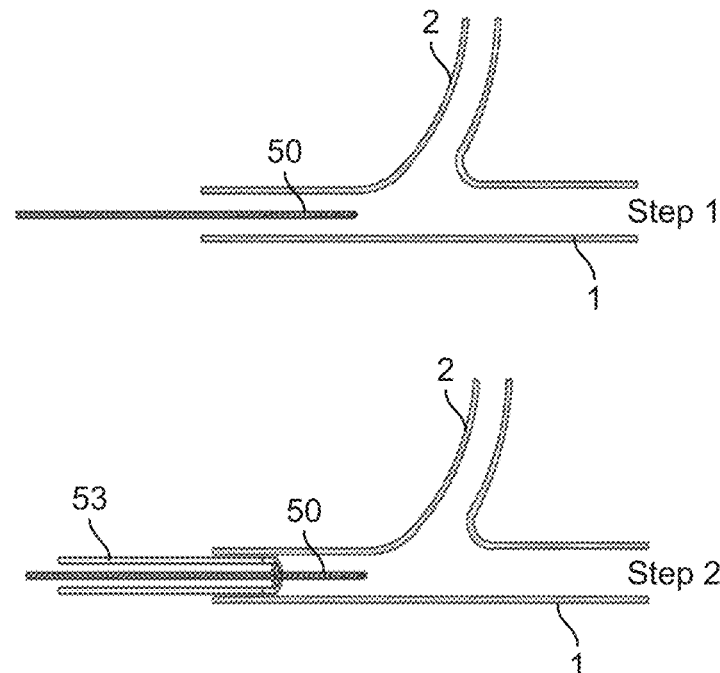
FIGS. 25-30 illustrate the delivery sequence of a preferred embodiment in eight steps.
Figure 26:
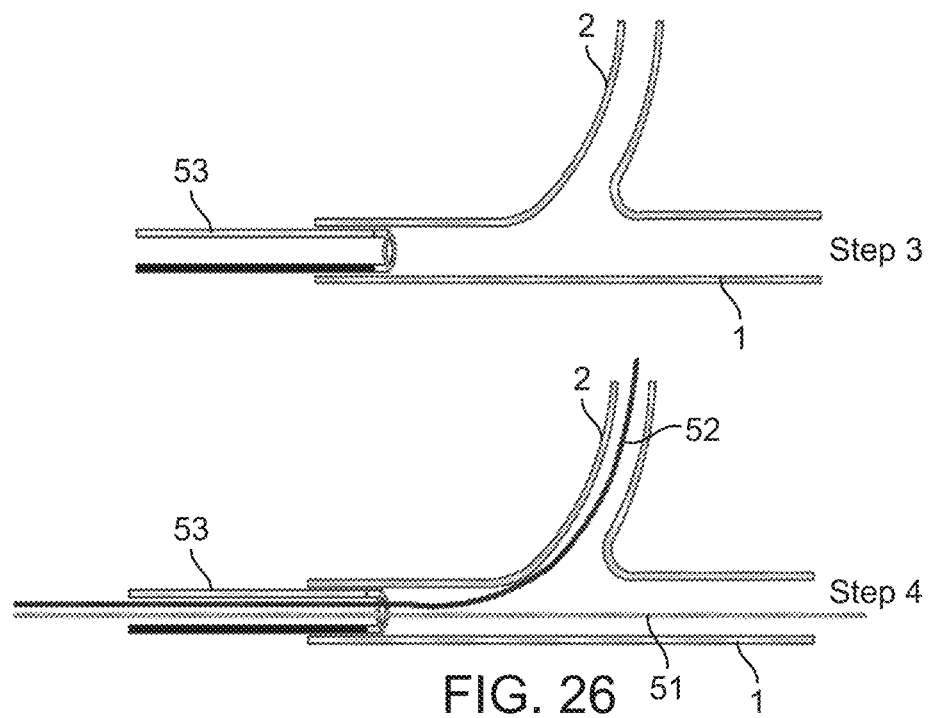
Figure 27:
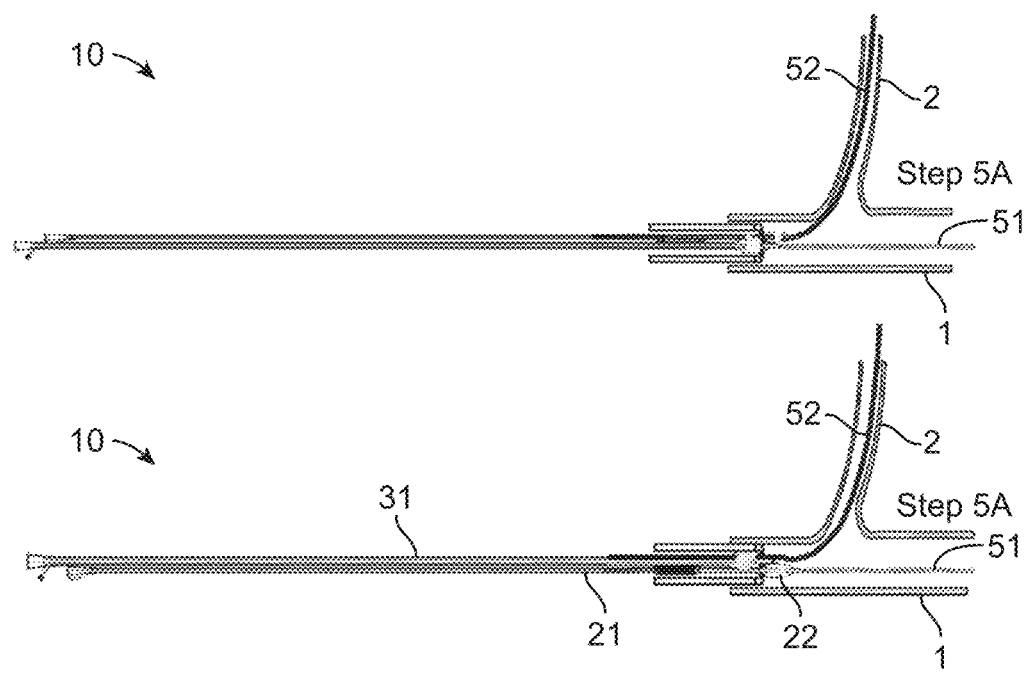
Figure 28:
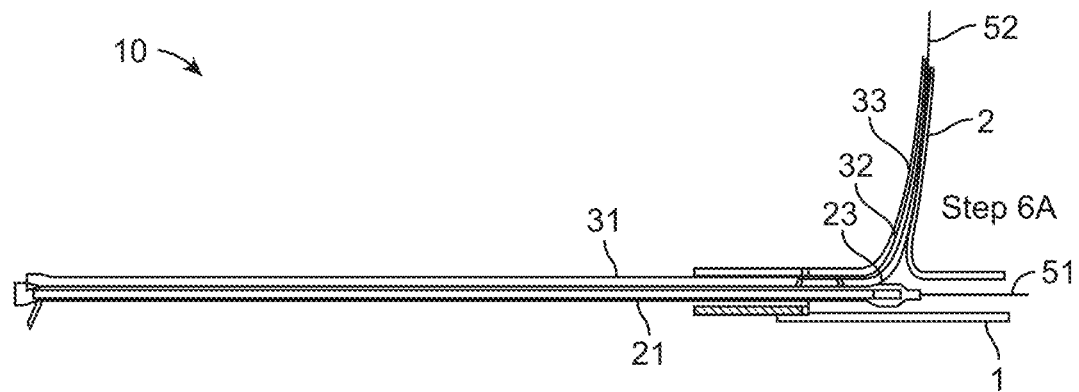
Figure 28:
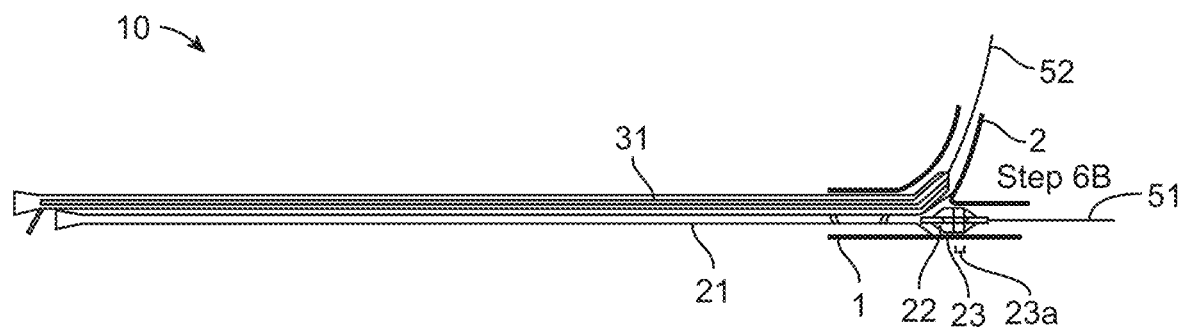
Figure 29:
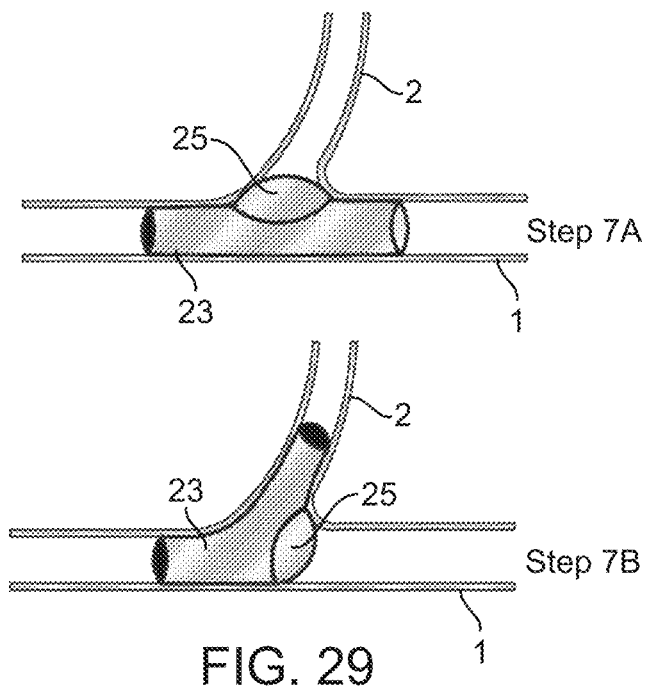
Figure 30:
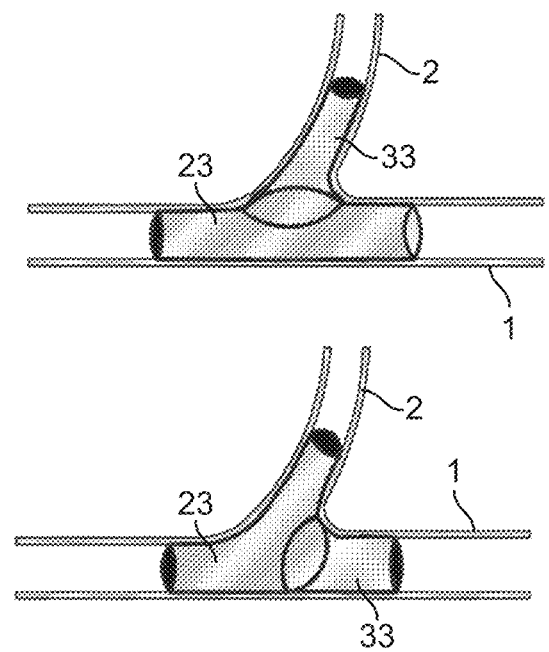

FIGS. 21-24 illustrate commercially available catheters that can be used with an alternative embodiment where in the mother catheter 21 is provided to the operator with a mother stent 23 (not shown) that is crimped on the distal portion of the mother catheter balloon 22a. The proximal portion 23b of the mother stent 23 is uncrimped. The operator can mount any commercially available catheter or balloon on a wire through the end of the mother stent proximal portion 23b and exit out the side hole 25 of the mother stent 23. See FIG. 36. The operator can align the catheters to suit the patient's anatomy and crimp the proximal portion 23b of the mother stent 23. The operator can crimp the stent 23 tightly so that the catheters do not move relative to each other. It is possible for the operator to place the catheters at the bifurcation and if necessary pullback on the commercially available catheter to adjust the alignment if necessary. Then the operator can gently push the system distally to ensure complete apposition. FIG. 21 illustrates a distal daughter catheter 31 with a rapid exchange design and a proximal mother catheter 21 with an over the wire design. FIG. 22 illustrates a distal daughter catheter 31 with an over the wire design and a proximal mother catheter 21 with a rapid exchange design. FIG. 23 illustrates a dual rapid exchange design. FIG. 24 illustrates a dual over the wire design.

Alternative embodiments of commercially available catheters that are single use devices for treating a single vessel, but can be mated together in various combinations with a polymer sleeve. The operator chooses the two catheters for the patient's anatomy then slides a sized polymer sleeve over both catheters from the distal ends. Once the operator has the catheters aligned the polymer sleeve can be treated with a heat or light source to shrink and bond the two catheters together with friction. The polymer sleeve is made of typical polymers that can act as shrink wrap when treated with a heat or light source. The polymer of the polymer sleeve for example could be manufactured with polyolefin a chemical used in manufacturing shrink wrap. The polymer sleeve would not crosslink or covalently attach to the catheters, several types of polymers are commercially available and have the requisite properties, thin, strong, not adhesive, and reaction times to their source of ten minutes or less. The polymer sleeves are typically 15 centimeters in length and have various diameters to suit typical catheter diameters 4 French to 20 French. The operator can test that the bond is holding by applying slight pressure prior to the procedure. If the polymer sleeve does not hold tightly the operator may elect to use a smaller diameter polymer sleeve or use more than one polymer sleeve by placing the polymer sleeves adjacent to each other. Alternatively, several smaller sleeves from 1 to 10 centimeters in length could be placed over several different portions of the catheters.

FIGS. 25-30 illustrate the delivery sequence of a preferred embodiment in eight steps. Step 1 illustrates the introduction of a 0.035 inch guidewire 50 up to the bifurcation. Step 2 illustrates the tracking of a guide catheter 53 over the guidewire 50. Step 3 illustrates the removal of the guidewire 50 and placement position of the guide catheter 53. Step 4 illustrates the tracking and placement of a rapid exchange compatible wire 52 in the daughter vessel 2 and an over the wire compatible wire 51 in the mother vessel 1. Step 5A & 5B illustrate tracking of the catheter system 10 distally over both the guidewires. Step 6A illustrates the inflation of the daughter balloon 32 and placement of the daughter stent 33 and partial deployment of the mother stent 23. Step 6B illustrates the inflation of the mother balloon 22 to place the distal portion 23a of the mother stent 23 in the mother vessel 1. Step 7A illustrates the mother stent 23 in the main branch with side hole 25 facing the daughter vessel 2. Step 7B illustrates a bifurcated stent partially in the daughter vessel 2 and the mother vessel 1 where a side hole 25 of the mother stent 23 opens toward the main branch vessel 1.

In an alternative embodiment the delivery catheter mother balloons having tapered ends to accommodate balloons and stents with non-uniform profiles. For example, the proximal end of the daughter vessel stent may be designed to have a larger circumference than the distal end to compensate for the natural bifurcation anatomy. The daughter vessel balloon would likewise have a taper to properly expand the stent and ensure complete apposition. Additionally, it is possible to design the mother stent to expand differentially along its profile to compensate for a larger arterial diameter at the carina or ostium. In other words, the proximal and distal ends of the mother vessel balloon and mother vessel stent would be smaller in circumference while the center portion of the mother vessel stent would have a larger circumference.

In an alternative embodiment the mother vessel balloon having tapered ends to accommodate the distal balloon catheter portion and guidewire lumen. Further, the mother vessel balloon is designed for differential expansion to accommodate natural vessel anatomy.

In a preferred embodiment wherein the distal (daughter) balloon catheter portion is crimped with a half stent on a rapid exchange type design catheter. The daughter vessel stent is 4-20 millimeter and the daughter vessel balloon is approximately twice as long in length. The mother vessel stent 10-30 millimeter is differentially crimped to allow independent operation of the daughter balloon catheter portion. The distal portion of the mother vessel stent is crimped tightly enough to keep the entire stent from unintentionally dislodging during the procedure. The proximal portion of the mother vessel stent is crimped just tightly enough to reduce the crossing profile and allow the daughter balloon catheter portion to be moved distal or proximal relative to the mother balloon catheter portion. The proximal (mother) balloon catheter portion is an over the wire type design with the mother vessel balloon about 3 centimeters proximal to the daughter vessel balloon.

In an alternative embodiment a stent is designed to allow differential expansion of the middle portion of the stent relative to the proximal and distal ends. In particular, the design facilitates the placement of the stent across a bifurcation lesion in the mother vessel because it has a larger circumference in the middle portion relative to the ends than a stent with a constant profile. Further, the profile can be adjusted so that the largest circumference can be placed proximal or distal to the midpoint of the stent. In the particular embodiment the largest circumference is distal to the midpoint of the stent, but could be easily reversed for variable patient anatomy.

Figure 31:
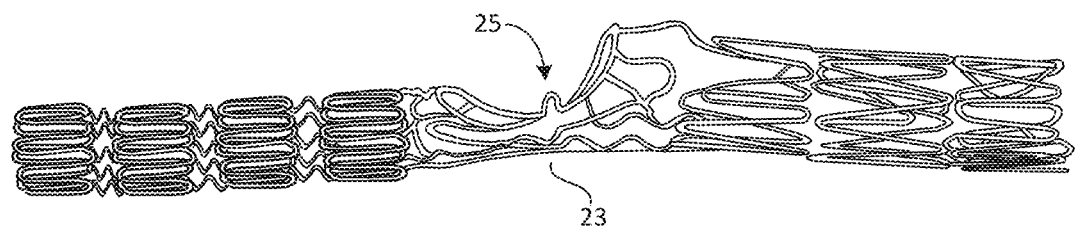
FIG. 31 is a photograph of a preferred embodiment with a bifurcation stent partially crimped.
Figure 32:
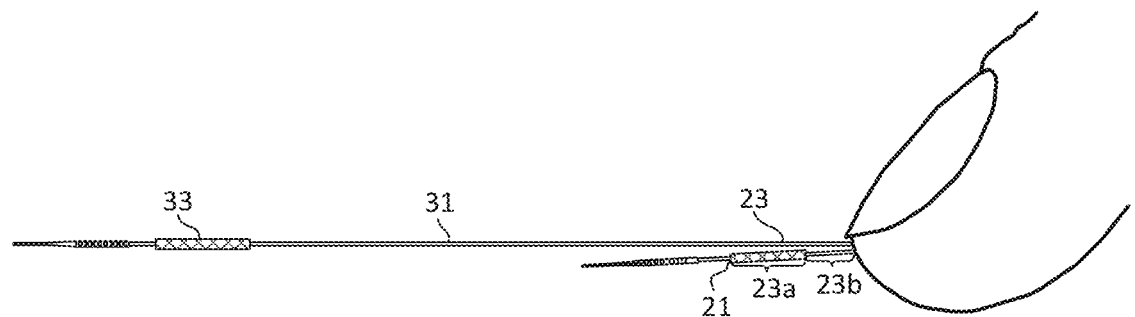
FIG. 32 is a photograph of a preferred embodiment with a bifurcation stent partially crimped with a second catheter threaded through the bifurcation stent hole.
Figure 33:
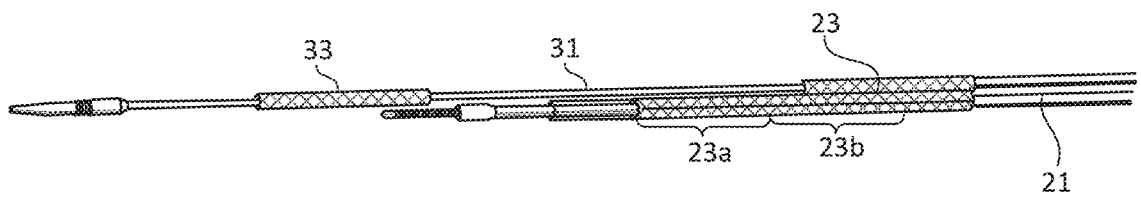
FIG. 33 is a photograph of a preferred embodiment with a bifurcation stent partially crimped with a second catheter threaded through the bifurcation stent hole.
Figure 34:
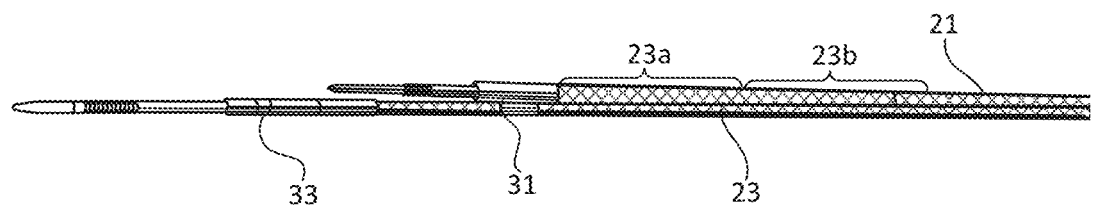
FIG. 34 is a photograph of a preferred embodiment with the system fully aligned and fully crimped.

Partial crimping has the following key features that make it possible to maintain sufficient stent retention during delivery and placement and still allows the secondary system adjustability and deliverability. FIG. 31 is a partially crimped bifurcation stent prior to placement on any balloon catheter. FIGS. 32-34 illustrate an embodiment of the present invention in three steps. First, the bifurcation stent 23 is partially crimped over approximately one-third the distal portion 23a of the bifurcation stent on to the mother catheter 21 and the daughter catheter 31 is loaded through the mother catheter 21 and mother stent 23 where the daughter stent 33 can be crimped separately. Second, the daughter stent 33 is crimped and pulled back proximally to align the proximal end of the daughter stent 33 near the distal end of the mother stent 23. Third, the proximal portion of the mother stent 23b can be crimped to reduce the outer diameter, yet still allow independent movement of the two catheters relative to each other.

Figure 35:
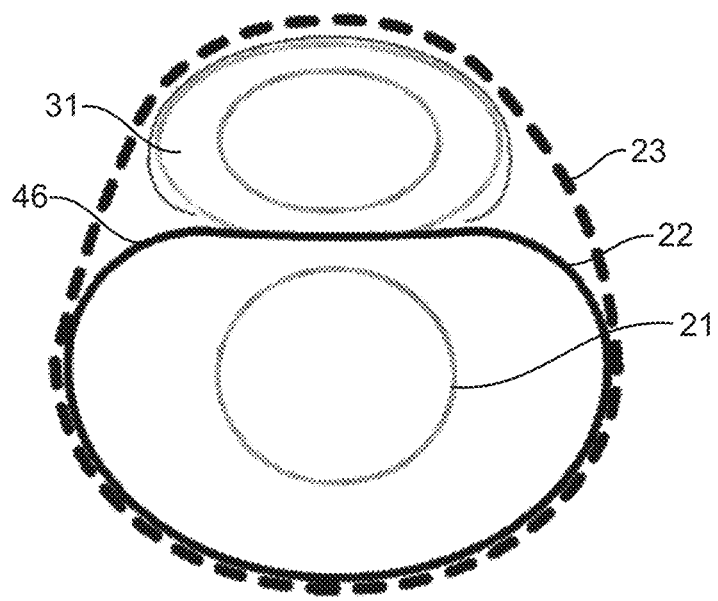
FIG. 35 is a cross sectional view of a differentially crimped stent on two catheters.
Figure 36:
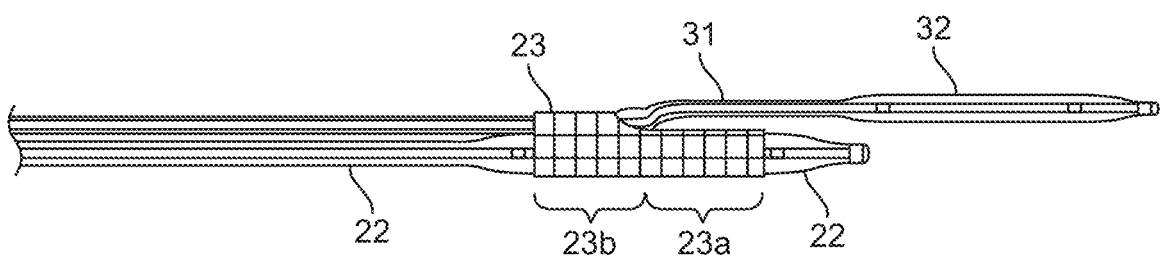
FIG. 36 is a profile view of a stent mounted on two balloon catheters.
Figure 37:
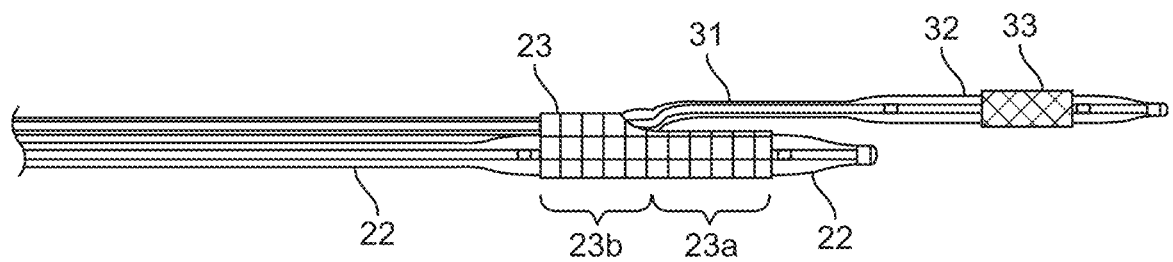
FIG. 37 is a profile view of a stent mounted on two balloon catheters.

FIG. 35 illustrates a cross section of a daughter balloon catheter 31 without a daughter stent. The daughter catheter 31 is on top of the mother catheter 21. The mother stent 23 is differentially crimped around the mother catheter balloon 22 and daughter catheter 31 because the daughter catheter 31 profile is smaller than the mother catheter 21 profile. The differential crimping is non-uniform and can create various cross sectional shapes to accommodate different catheter designs, balloon designs, and stent designs. For example, pear shaped or a figure eight are possible configurations. The current embodiment is designed to reduce the profile as much as possible. In one preferred method of manufacturing, a protective sheet 46 is placed between the two catheters. The protective sheet 46 only needs to cover the portions that will come in contact during the crimping process, then the protective sheet 46 can be removed. FIG. 36 illustrates a side view of the mother stent 23 mounted on the mother catheter balloon 22 and the daughter catheter 31 mounted on the mother catheter 21 through the mother stent 22. The distal portion 23a of the mother stent 23 will be crimped under standard conditions to hold stent firmly to the mother balloon 22 and mother catheter 21. The proximal portion 23b of the mother stent 23 is partially crimped to reduce the profile, but still allows the daughter catheter 31 freedom to move proximal or distal relative to the mother catheter 21. This embodiment illustrates that the stent 23 is differentially crimped in both the circumferential and longitudinal direction. The amount of crimping will be determined by the stent design and size, catheter dimensions, and balloon dimensions; thus the crimping is differential along the longitudinal axis. FIG. 37 illustrates a side view of the mother stent 23 mounted on the mother catheter balloon 22 and the daughter catheter 31 mounted on the mother catheter 21 through the mother stent 23. The daughter catheter 31 also includes a stent 33 that can be crimped under standard conditions. The distal portion 23a of the mother stent 23 will be crimped under standard conditions to hold stent firmly to the mother balloon 22 and mother catheter 21. In one experiment, this arrangement was tested to determine the strength of the distal crimping of the mother stent 23 by pulling the daughter catheter 31 and daughter stent 33 proximally; the results were that the daughter catheter 31 successfully passed through the crimped mother stent 23 and still retained the daughter stent 33 as well.

Additional features may be utilized during the crimping process such as adding a slight positive internal pressure to the balloon so that the final balloon surface pillows about 0.002 inch beyond the outer diameter of the stent. This process can yield a design that protects the stent from engaging with the vessel thus reducing friction and improving stent retention at the same time. Further, this process improves safety and reduces trauma to the vessel.

While the above embodiment discloses a bifurcation stent that is crimped at or about its distal half; this is not a limitation. The stent could be differentially crimped along its axis depending upon stent design, for example; if a hole in the side of a stent was not centered along the axis. It may be preferential to have the distal crimped portion of the bifurcation stent extend just distal of the hole that the daughter catheter to pass through. Alternatively, the distal crimped portion could extend partially or entirely over the hole that the daughter catheter passes through.

While the invention has been described in conjunction with specific embodiments and examples thereof, it is evident that many alternatives, modifications and variations will be apparent to those skilled in the art upon reading the present disclosure. Accordingly, it is intended to embrace all such alternatives, modifications and variations that fall within the spirit and broad scope of the appended claims.

What is claimed is:

1. A method for fabricating a catheter assembly for treating a bifurcated vessel having a mother vessel and a daughter vessel, the method comprising:

positioning a daughter catheter that includes a daughter expandable member to extend distally through a proximal portion of a mother stent disposed over a mother expandable member coupled to a mother catheter, and out through a side hole of the mother stent before disposing the mother stent in the bifurcated vessel, so that the daughter expandable member is disposed distal to the side hole and a distal end of the mother expandable member prior to and during advancement of the mother and daughter catheters in the respective mother and daughter vessels; and partially crimping the mother stent to the mother expandable member so as to accommodate proximal and distal movement of the daughter catheter relative to the mother stent crimped to the mother expandable member prior to and during advancement of the mother and daughter catheters in the respective mother and daughter vessels.

2. The method of claim 1, wherein the partially crimping of the mother stem to the mother expandable member comprises:

positioning a protective sheath between a portion of the mother expandable member and a portion of the daughter catheter expandable member to separate the respective portions; and crimping the portion of the mother stent around the protective sheath and the portion of the daughter catheter separated from the portion of the mother stent by the protective sheath.

3. The method of claim 1, wherein the partially crimping of the mother stent to the mother expandable member comprises crimping a distal portion of the mother stent to the mother expandable member prior to the positioning of the daughter catheter.

4. The method of claim 1, wherein the partially crimping of the mother stent forms a portion of the mother stent proximal to the side hole to have a pear shape or a figure eight shape.

5. The method of claim 1, further comprising crimping a daughter stent to the daughter expandable member.

6. The method of claim 5, further comprising, after the partially crimping of the mother stent to the mother expandable member, retracting the daughter catheter proximally to align a proximal end of the daughter stent near a distal end of the mother stent crimped to the mother expandable member.

* * * * *

UNITED STATES PATENT AND TRADEMARK OFFICE
CERTIFICATE OF CORRECTION

PATENT NO. : 11,000,392 B2  
APPLICATION NO. : 15/661975  
DATED : May 11, 2021  
INVENTOR(S) : Bourang et al.

Page 1 of 1

It is certified that error appears in the above-identified patent and that said Letters Patent is hereby corrected as shown below:

On the Title Page

Item (60), in "Related U.S. Application Data", in Column 1, Line 1, delete "(60)" and insert --(63)-- therefor In the Specification In Column 10, Line 14, delete "and daughter 31 balloon 32." and insert --31 and daughter balloon 32.-- therefor In Column 10, Line 16, delete "32" and insert --31-- therefor In Column 10, Line 18, delete "32" and insert --31-- therefor In Column 10, Line 19, delete "32" and insert --31-- therefor In Column 10, Line 21, delete "port 40 5 centimeters." and insert --port 40.-- therefor In Column 14, Line 23, delete "22." and insert --23.-- therefor In the Claims In Column 16, Line 2, in Claim 2, delete "stem" and insert --stent-- therefor Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*